US009196468B2

(12) United States Patent
Campbell et al.

(10) Patent No.: US 9,196,468 B2
(45) Date of Patent: Nov. 24, 2015

(54) METHOD AND SYSTEM FOR INTRODUCING MAKE-UP FLOW IN AN ELECTROSPRAY ION SOURCE SYSTEM

(71) Applicant: DH Technologies Development Pte. Ltd., Singapore (SG)

(72) Inventors: John L. Campbell, Milton (CA); Thomas Covey, Richmond Hill (CA); Yves LeBlanc, Newmarket (CA); Bradley B. Schneider, Bradford (CA)

(73) Assignee: DH Technologies Development Pte. Ltd., Singapore (SG)

( * ) Notice: Subject to any disclaimer, the term of this patent is extended or adjusted under 35 U.S.C. 154(b) by 0 days.

(21) Appl. No.: 14/395,705

(22) PCT Filed: May 17, 2013

(86) PCT No.: PCT/IB2013/000976
§ 371 (c)(1),
(2) Date: Oct. 20, 2014

(87) PCT Pub. No.: WO2013/171574
PCT Pub. Date: Nov. 21, 2013

(65) Prior Publication Data
US 2015/0076342 A1 Mar. 19, 2015

Related U.S. Application Data

(60) Provisional application No. 61/649,037, filed on May 18, 2012.

(51) Int. Cl.
*B05B 5/025* (2006.01)
*G01N 30/02* (2006.01)
*H01J 49/00* (2006.01)
*F23D 11/22* (2006.01)
*H01J 49/16* (2006.01)
*G01N 27/62* (2006.01)
*H01J 49/04* (2006.01)

(52) U.S. Cl.
CPC ............ *H01J 49/165* (2013.01); *G01N 27/622* (2013.01); *H01J 49/0081* (2013.01); *H01J 49/0431* (2013.01)

(58) Field of Classification Search
USPC ............ 250/281, 282, 288, 423 R, 424, 425, 250/432 E, 435, 438, 526; 239/3, 5, 8–10, 239/20–23, 36, 124, 125, 193, 194, 265.17, 239/299, 317, 365, 602, 690, 692, 695, 696, 239/697.698, 704, 705, 707, 708; 422/69, 422/70, 81, 93, 207, 208, 296, 298, 405, 422/408, 412, 417, 419, 423, 500–504, 507, 422/508.528, 529; 73/53.01, 61.55
See application file for complete search history.

(56) References Cited

U.S. PATENT DOCUMENTS 6,426,997 B1 7/2002 Fuchs et al.
6,744,046 B2 * 6/2004 Valaskovic et al. ........... 250/288
(Continued)

FOREIGN PATENT DOCUMENTS

WO 2007-002141 1/2007

OTHER PUBLICATIONS

International Search Report from International Patent Application No. PCT/IB2013/000976, dated Oct. 16, 2013.

*Primary Examiner* — Bernard E Souw

(57) ABSTRACT

An electrospray ion source method and system is provided for detecting emitter failure comprising a liquid chromatography column suitable for chromatographic separation of a sample. The column can have an inlet for receiving the sample; and an outlet for ejecting the sample. A make-up flow channel is provided for introducing make-up flow of liquid to the sample post-column, wherein the make-up flow normalizes the spray current. An electrospray ionization source is provided having one or more electrospray ionization emitter nozzles for receiving the make-up flow containing sample. A power supply can provide a voltage to the one or more emitter nozzles, and a measurement device can measure and monitor the spray current.

20 Claims, 26 Drawing Sheets

(56) References Cited

U.S. PATENT DOCUMENTS

| | | | |
|---|---|---|---|
| 2006/0193748 A1* | 8/2006 | Tai et al. | 422/70 |
| 2006/0285999 A1* | 12/2006 | Timperman | 422/100 |
| 2007/0023640 A1* | 2/2007 | Davidson et al. | 250/288 |
| 2008/0173808 A1* | 7/2008 | Ramanathan et al. | 250/282 |
| 2008/0257019 A1 | 10/2008 | Rosati et al. | |
| 2008/0315083 A1* | 12/2008 | Lubda et al. | 250/288 |
| 2009/0152371 A1 | 6/2009 | Stark et al. | |

* cited by examiner

Figure 6 Integrated micro-machined system

Figure 7 Planar Chip column with built in makeup channel

Five LC gradient runs each covering a solvent composition range of 100% aqueous (0.1% formic acid) to 100% organic (acetonitrile). The broad range of spray current measurements within a single sample negates its value as means to detect nozzle failure.

Nozzles most commonly fail during high aqueous portion of gradient. Under these conditions, the measured spray current drops around 35 nA. This Flow Mode  Conserved. Total Flowrate = 0.4 uL/min Gradient Table
| Time (min) | %A | %B |
|---|---|---|
| 0 | 98 | 2 |
| 2 | 98 | 2 |
| 10 | 20 | 80 |
| 10.2 | 2 | 98 |
| 12 | 2 | 98 |
| 12.2 | 98 | 2 |
| 20 | 98 | 2 |

Mobile Phases
Solvent A    0% Acetonitrile | 0.1% F.A.
Solvent B    100% Acetonitrile | 0.1% F.A.

Figure 12

Figure 16  Exploded view of the differential mobility spectrometer (DMS) used in these experiments as coupled to a 5500 QTRAP mass spectrometer.

Figure 17  Cross-sectional view of the DMS depicting the relevant components and gas flows Figure 18  Structures of the two most energetically favored sites of protonation for 4-aminobenzoic acid formed by positive-mode electrospray ionization.

Figure 19  Results for three individual aminobenzoic acid isomers analyzed by ESI(+)-DMS-MS. Only the 4-aminobenzoic acid isomer yields two distinct peaks upon analysis.

Figure 22 MS/MS spectra (CE = 30 eV$_{Lab}$) obtained for Q1-selected ions of m/z 138 ([M+H]+ of 4-ABA) at (a) CV = -1.5V and (b) CV = -7.5V Figure 23 (a) DMS ionogram obtained before and after an HDX experiment on protonated 4-ABA formed by ESI(+); (b) ESI-MS recorded at CV = -7.5V before (pale trace) and during (dark) HDX; (c) ESI-MS recorded at CV = -1.5V before (pale trace) and during (dark trace) HDX

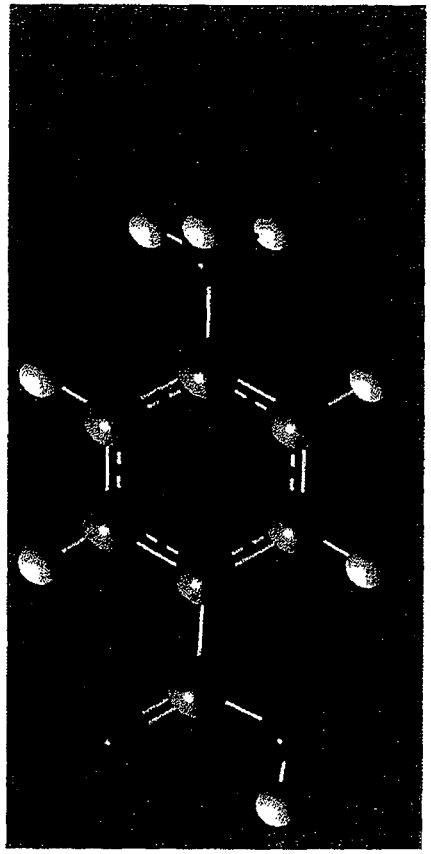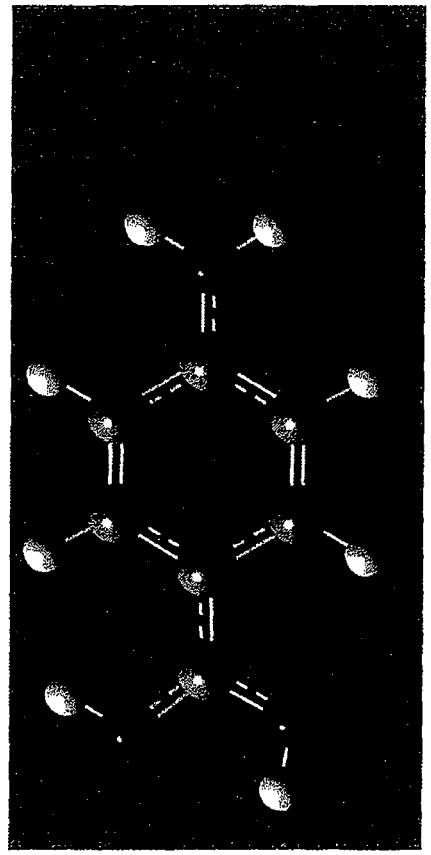
Figure 25  Calculated structures of both the (a) N-protonated and (b) O-protonated forms of 4-ABA, including the calculated dipole moments for each ion

| m/z | CV -7.5 V | -1.5 V |
|---|---|---|
| 138 | 23.3 | 1.2 |
| 121 | 8.9 | 0.0 |
| 120 | 7.1 | 100.0 |
| 103 | 1.0 | 0.0 |
| 94 | 31.0 | 43.1 |
| 93 | 26.4 | 11.3 |
| 92 | 4.5 | 57.5 |
| 77 | 100.0 | 85.0 |
| 75 | 4.5 | 0.0 |
| 65 | 46.6 | 40.1 |

Figure 26  Relative abundances (%) of each fragment ion resulting from the MS/MS (Collision energy = 30 $eV_{Lab}$) of m/z 138 precursor ions at CV = -7.5V and CV = -1.5V.

METHOD AND SYSTEM FOR INTRODUCING MAKE-UP FLOW IN AN ELECTROSPRAY ION SOURCE SYSTEM

RELATED APPLICATION

This application claims priority to U.S. provisional application No. 61/649,037, filed on May 18, 2012, which is incorporated herein by reference in its entirety.

FIELD

The applicants' teachings relate to a method and system for introducing make-up flow in an electrospray ion source system, and more specifically for detecting electrospray emitter failure and altering the protonation site of ions.

INTRODUCTION

In an electrospray ion source system, oftentimes there can be spontaneous failure of emitters due to the presence of precipitating samples and other fouling agents resulting in spray failure. Detection of spray failure can be problematic since during an LC run, there is a very large spray current range, for example, spanning from 1 nA to 150 nA from the beginning of a gradient to the end of the gradient making monitoring the ion current in this range ineffective. Accordingly, a need exists for reliably detecting electrospray emitter failure.

In addition, an ion mobility device, such as a differential mobility spectrometer (DMS) in conjunction with electrospray provides the capability to separate ions at atmospheric pressure prior to mass analysis. But, oftentimes separating closely related ions, such as isoforms and isomers can be difficult. Accordingly, a need exists for an added degree of selectivity in separating closely related ions.

SUMMARY

In view of the foregoing, in various embodiments, the applicants' teachings provide an electrospray ion source system for detecting emitter failure. In various embodiments, the system comprises a liquid chromatography column suitable for chromatographic separation of a sample. In various aspects, the column can have an inlet for receiving the sample and an outlet for ejecting the sample. In various embodiments, the system can comprise a make-up flow channel for introducing a make-up flow of liquid to the sample post-column, wherein the make-up flow normalizes the spray current. In various aspects, an electrospray ionization source can be provided having one or more emitter nozzles for receiving the make-up flow containing sample. In various embodiments, there can comprise a power supply for providing a voltage to the one or more emitter nozzles and a measurement device for measuring and monitoring the spray current of the one or more emitter nozzles.

In various embodiments, the liquid chromatography column can be micromachined on a first substrate. In various aspects, the make-up flow channel can be micromachined on a second substrate. In various embodiments, the system can further comprise a connector for connecting the first substrate to the second substrate.

In various embodiments, the make-up flow can be a dilute electrolyte. In various aspects, the make-up flow can be a solvent without electrolyte. In various embodiments, the make-up flow channel can comprise a tee junction. In various embodiments, the make-up flow channel can comprise but is not limited to a y junction, concentric tubes, microfabricated channels, two arrays that are coupled, and a mixing tee junction on a substrate.

In various embodiments, the one or more nozzles can comprise an array of emitters. In various aspects, the one or more nozzles can comprise a plurality of an array of emitters.

In various embodiments, the array of emitters or one or more of the plurality of the array of emitters can be replaced when the spray current exceeds the normalized spray current limits indicating nozzle failure.

In various aspects, the connector can comprise a transfer capillary. In various embodiments, the measurement device can comprise an ammeter.

In various embodiments, there can be provided a positioning device for positioning the array of emitters or one or more of the plurality of the array of emitters.

In various aspects, the system can comprise a mass spectrometer for analyzing the spray from one or more emitter nozzles.

In various embodiments, a method is provided for detecting emitter failure comprising providing liquid chromatography column suitable for chromatographic separation of a sample. In various aspects, the column can have an inlet for receiving the sample and an outlet for ejecting the sample. In various embodiments, a make-up flow channel can be provided for introducing a make-up flow of liquid to the sample post-column, wherein the make-up flow normalizes the spray current. In various embodiments, there can be provided an electrospray ionization source having one or more emitter nozzles for receiving the make-up flow containing sample. In various aspects, a power supply can be provided for providing a voltage to the one or more emitter nozzles and a measurement device can be provided for measuring and monitoring the spray current of the one or more emitter nozzles.

In various aspects, the liquid chromatography column can be micromachined on a first substrate. In various embodiments, the make-up flow channel can be micromachined on a second substrate. In various aspects, the method can further comprise providing a connector for connecting the first substrate to the second substrate.

In various embodiments, the make-up flow can be a dilute electrolyte. In various embodiments, the make-up flow can be a solvent without electrolyte. In various aspects, the make-up flow channel can comprise a tee junction. In various embodiments, the make-up flow channel can comprise but is not limited to a y junction, concentric tubes, microfabricated channels, two arrays that are coupled, and a mixing tee junction on a substrate.

In various embodiments, the one or more nozzles can comprise an array of emitters. In various aspects, the one or more nozzles can comprise a plurality of an array of emitters.

In various embodiments, the array of emitters or one or more of a plurality of an array of emitters can be replaced when the spray current exceeds the normalized spray current limits indicating nozzle failure.

In various aspects, the connector can comprise a transfer capillary. In various embodiments, the measurement device can comprise an ammeter.

In various embodiments, a positioning device can be provided for positioning the array of emitters or one or more of the plurality of the array of emitters.

In various aspects, the method further comprises providing a mass spectrometer for analyzing the spray from one or more emitter nozzles.

In various embodiments, an electrospray ion source system is provided for altering the site of protonation of ions. In various aspects, an electrospray ion source system is provided for altering the site of charging of ions. One skilled in the art can appreciate that one can alter the site of charging a molecule in a number of ways including but not limited to changing the site of protonation, changing the site of deprotonation, changing the site of a positive adduct ion, changing the site of a negative adduct ion, changing the site of a radical cation (conventional or distonic), changing the site of a radical anion (conventional or distonic), or other forms of charging as known in the art. In various aspects, the system comprises a liquid chromatography column suitable for chromatographic separation of a sample. In various embodiments, the column can have an inlet for receiving the sample and an outlet for ejecting the sample. In various aspects, a make-up flow channel can be provided for introducing a make-up flow of liquid to the sample post-column, wherein the make-up flow alters the site of protonation of ions. In various embodiments, the make-up flow alters the site of charging of ions. In various aspects, one skilled in the art can appreciate that one can alter the site of charging a molecule in a number of ways including but not limited to changing the site of protonation, changing the site of deprotonation, changing the site of a positive adduct ion, changing the site of a negative adduct ion, changing the site of a radical cation (conventional or distonic), changing the site of a radical anion (conventional or distonic), or other forms of charging as known in the art. In various embodiments, an electrospray ionization source can be provided having one or more emitter nozzles for receiving the make-up flow containing sample. In various aspects, a power supply can be provided for providing a voltage to the one or more emitter nozzles. In various embodiments, an ion mobility device, including but not limited to low field mobility, DMA, etc., can be provided for separating the ions. In various embodiments, a differential ion mobility spectrometer can be provided for separating the ions.

In various aspects, the liquid chromatography column can be micromachined on a first substrate. In various embodiments, the make-up flow channel can be micromachined on a second substrate.

In various embodiments, the system can further comprise a connector for connecting the first substrate to the second substrate. In various aspects, the make-up flow can comprise an aprotic solvent. In various embodiments, the make-up flow can comprise a protic solvent. In various aspects, the make-up flow channel can comprise a tee junction. In various embodiments, the make-up flow channel can comprise but is not limited to a y junction, concentric tubes, microfabricated channels, two arrays that are coupled, and a mixing tee junction on a substrate.

In various embodiments, the one or more nozzles can comprise an array of emitters. In various aspects, the one or more nozzles can comprise a plurality of an array of emitters.

In various aspects, the connector can comprise a transfer capillary. In various embodiments, the system can further comprise a positioning device for positioning the array of emitters or one or more of the plurality of the array of emitters.

In various embodiments, the system can further comprise a mass spectrometer for analyzing the ions from the differential mass spectrometer.

A method for altering the site of protonation of ions is provided. In various embodiments, the method can comprise providing a liquid chromatography column suitable for chromatographic separation of a sample. In various aspects, the column can have an inlet for receiving the sample and an outlet for ejecting the sample. In various embodiments, the method can comprise providing a make-up flow channel for introducing a make-up flow of liquid to the sample post-column, wherein the make-up flow alters the site of protonation of ions. In various aspects, the make-up flow alters the site of charging of ions. One skilled in the art can appreciate that one can alter the site of charging a molecule in a number of ways including but not limited to changing the site of protonation, changing the site of deprotonation, changing the site of a positive adduct ion, changing the site of a negative adduct ion, changing the site of a radical cation (conventional or distonic), changing the site of a radical anion (conventional or distonic), or other forms of charging as known in the art. In various aspects, an electrospray ionization source can be provided having one or more emitter nozzles for receiving the make-up flow containing sample. In various embodiments, a power supply can be provided for providing a voltage to the one or more emitter nozzles. In various embodiments, an ion mobility device, including but not limited to low field mobility, DMA, etc., can be provided for separating the ions. In various aspects, a differential mobility spectrometer can be provided for separating the ions.

In various embodiments, the liquid chromatography column can be micromachined on a first substrate. In various aspects, the make-up flow channel can be micromachined on a second substrate. In various embodiments, the method can further comprise providing a connector for connecting the first substrate to the second substrate.

In various aspects, the make-up flow can comprise an aprotic solvent. In various embodiments, the make-up flow can comprise a protic solvent. In various aspects, the make-up flow channel can comprise a tee junction. In various embodiments, the make-up flow channel can comprise but is not limited to a y junction, concentric tubes, microfabricated channels, two arrays that are coupled, and a mixing tee junction on a substrate.

In various embodiments, the one or more nozzles can comprise an array of emitters. In various aspects, the one or more nozzles can comprise a plurality of an array of emitters.

In various embodiments, the connector can comprise a transfer capillary. In various aspects, the method can further comprise providing a positioning device for positioning the array of emitters or one or more of the plurality of the array of emitters.

In various embodiments, an ion mobility device, including but not limited to low field mobility, DMA, etc., can be provided for separating the ions. In various embodiments, the method can comprise providing a mass spectrometer for analyzing the ions from the differential mobility spectrometer.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

FIG. 12 shows an analytical gradient according to various embodiments of the applicant's teachings.

FIG. 20 (c) shows a DMS ionogram obtained during ESI (+)-MS/MS analysis of 4-ABA sprayed from a 50% acetonitrile, 50% water solution.

FIG. 21 (b) shows a DMS ionogram obtained during ESI (+)-MS/MS analysis of 4-ABA sprayed from a 50% methanol, 50% water solution.

FIG. 21 (c) shows a DMS ionogram obtained during ESI (+)-MS/MS analysis of 4-ABA sprayed from a 95% methanol, 5% water solution.

FIG. 21 (d) shows a DMS ionogram obtained during ESI (+)-MS/MS analysis of 4-ABA sprayed from a 25% acetonitrile, 75% water solution.

FIG. 21 (e) shows a DMS ionogram obtained during ESI (+)-MS/MS analysis of 4-ABA sprayed from a 50% acetonitrile, 50% water solution.

FIG. 21 (f) shows a DMS ionogram obtained during ESI (+)-MS/MS analysis of 4-ABA sprayed from a 95% acetonitrile, 5% water solution.

FIG. 22 (b) shows the MS/MS spectrum (CE=30 eV lab frame) obtained for Q1-selected ions of m/z 138 ([M+H]+ of 4-ABA) at CV=−7.5V.

FIG. 23 (b) shows an ESI-MS spectrum recorded at CV=−7.5V before (pale trace) and during (dark) HDX.

FIG. 23 (c) shows an ESI-MS spectrum recorded at CV=−1.5V before (pale trace) and during (dark) HDX.

FIG. 24 (b) shows a DMS dispersion plot for m/z 138 ions that fragmented to form ions of m/z 138 in the MS/MS spectra.

FIG. 24 (c) shows a DMS dispersion plot for m/z 12 ions that fragmented to form ions of m/z 121 in the MS/MS spectra.

FIG. 24 (d) shows a DMS dispersion plot for m/z 138 ions that fragmented to form ions of m/z 103 in the MS/MS spectra.

FIG. 24 (e) shows a DMS dispersion plot for m/z 138 ions that fragmented to form ions of m/z 120 in the MS/MS spectra.

FIG. 24 (f) shows a DMS dispersion plot for m/z 138 ions that fragmented to form ions of m/z 92 in the MS/MS spectra.

FIG. 25 (a) shows the calculated structure and dipole moment of N-protonated 4-ABA molecule.

FIG. 25 (b) shows the calculated structure and dipole moment of O-protonated 4-ABA molecule.

FIG. 26 shows the relative abundances (%) of each fragment ion resulting from the MS/MS (Collision energy=30 eVLab) of m/z 138 precursor ions at CV=−7.5V and CV=−1.5V.

In the drawings, like reference numerals indicate like parts.

DESCRIPTION OF VARIOUS EMBODIMENTS

A method and system for detecting electrospray emitter failure is provided. It should be understood that the phrase "a" or "an" used in conjunction with the applicant's teachings with reference to various elements encompasses "one or more" or "at least one" unless the context clearly indicates otherwise.

Figure 1:
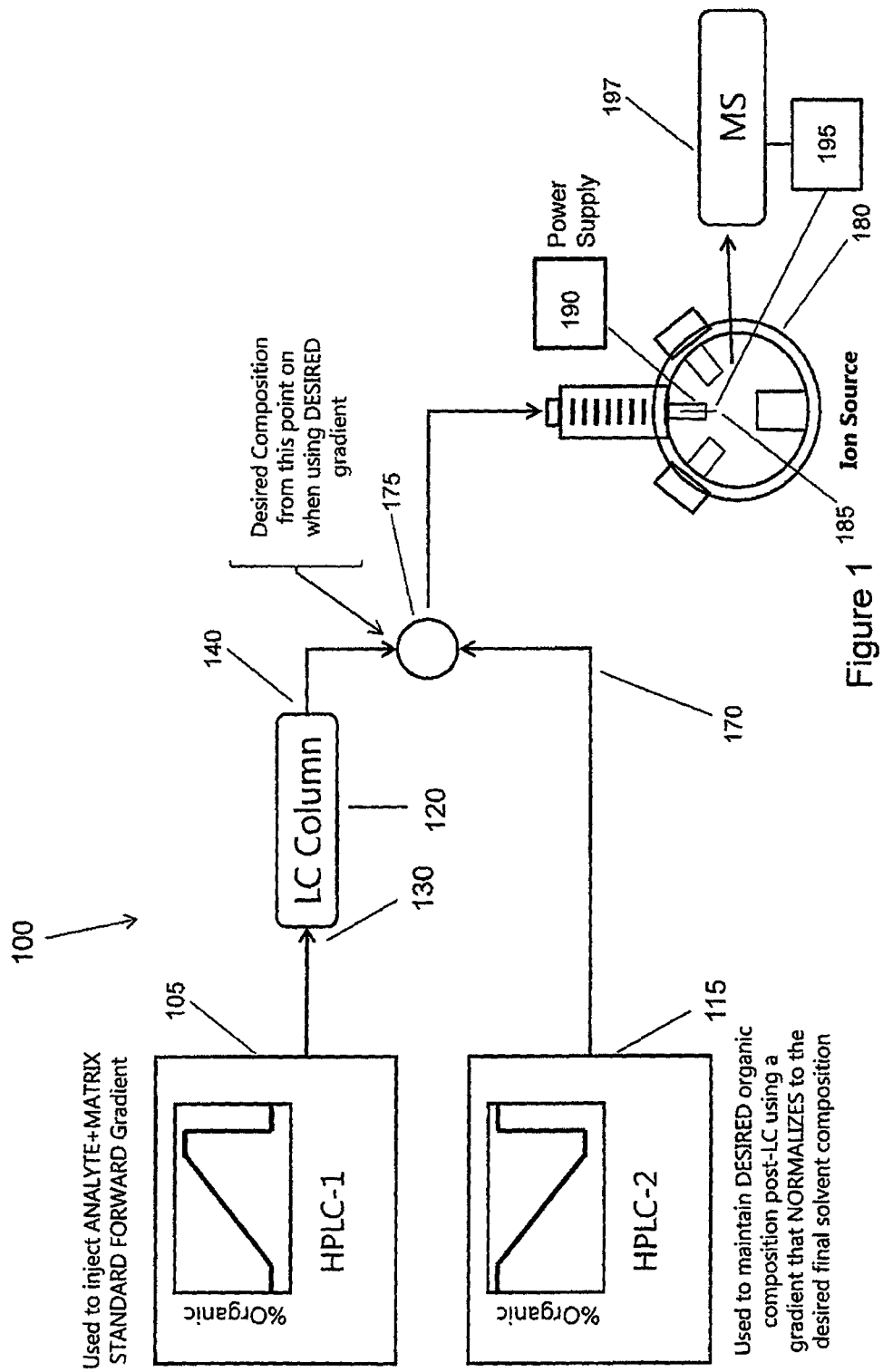
FIG. 1 is a schematic view of an electrospray system according to various embodiments of the applicant's teachings.
Figure 2:
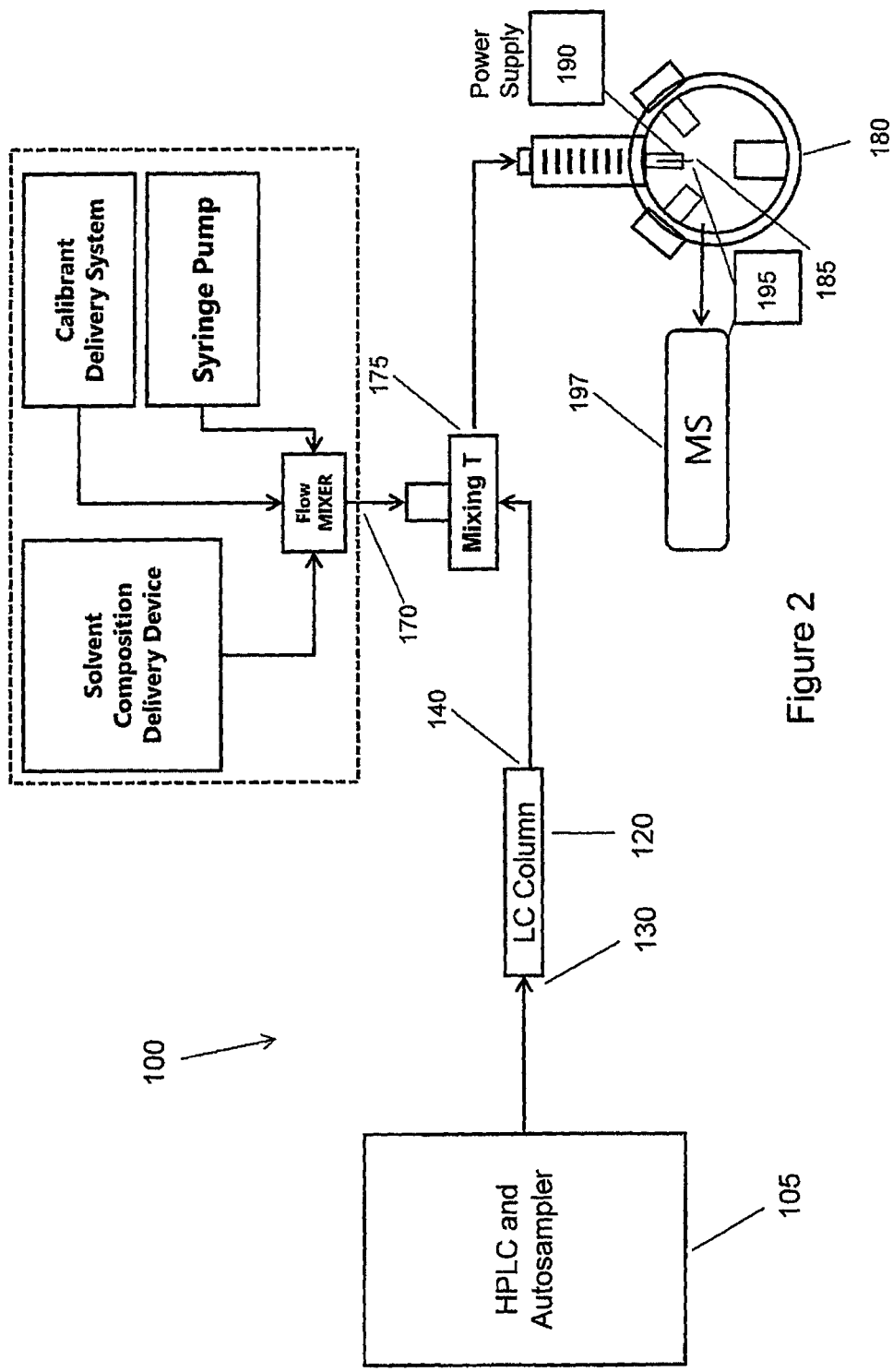
FIG. 2 is a schematic view of an electrospray system according to various embodiments of the applicant's teachings.

Reference is made to FIGS. 1 and 2, which show schematically, for example, an electrospray ion source system, generally indicated by reference number 100. As known in the art, an HPLC pump 105 can move mobile phase and sample through a liquid chromatography column 120. The system 100 comprises a liquid chromatography column 120 suitable for chromatographic separation of a sample. In various aspects, the column 120 can have an inlet 130 for receiving the sample and an outlet 140 for ejecting the sample. In various embodiments, the system can comprise a make-up flow channel 170 for introducing a make-up flow of liquid to the sample post-column, indicated at 175, wherein the make-up flow normalizes the spray current. In various embodiments, an HPLC pump 115, shown in FIG. 1, can be used to maintain the desired organic composition post-LC. In various embodiments, delivery systems can be used to deliver the make-up flow to the sample post-column, as shown in FIG. 2. In various aspects, an electrospray ionization source 180 can be provided having one or more emitter nozzles 185 for receiving the make-up flow containing sample. In various embodiments, the system can comprise, for example, a nanospray, a Turbo V™ source, or any other suitable electrospray ion source.

In various embodiments, there can comprise a power supply 190 for providing a voltage to the one or more emitter nozzles and a measurement device 195 for measuring and monitoring the spray current of the one or more emitter nozzles.

As shown in FIGS. 3 to 7, in various embodiments, the liquid chromatography column can be micromachined on a first substrate. In various aspects, the make-up flow channel can be micromachined on a second substrate. In various embodiments, the system can further comprise a connector for connecting the first substrate to the second substrate. In various aspects, the connector can comprise a transfer capillary.

In various embodiments, the make-up flow can be a dilute electrolyte. In various aspects, the make-up flow can be a solvent without electrolyte. In various embodiments, the make-up flow channel can comprise a tee junction. In various embodiments, the make-up flow channel can comprise but is not limited to a y junction, concentric tubes, microfabricated channels, two arrays that are coupled, and a mixing tee junction on a substrate.

In various embodiments, the one or more nozzles can comprise an array of emitters. In various aspects, the one or more nozzles can comprise a plurality of an array of emitters.

In various embodiments, the array of emitters or one or more of the plurality of the array of emitters can be replaced when the spray current exceeds the normalized spray current limits indicating nozzle failure.

In various embodiments, the measurement device can comprise an ammeter.

In various embodiments, there can be provided a positioning device for positioning the array of emitters or one or more of the plurality of the array of emitters.

In various aspects, the system can comprise a mass spectrometer 197 for analyzing the spray from one or more emitter nozzles.

In various embodiments, a method is provided for detecting emitter failure comprising providing liquid chromatography column 120 suitable for chromatographic separation of a sample. In various aspects, the column 120 can have an inlet 130 for receiving the sample and an outlet 140 for ejecting the sample. In various embodiments, a make-up flow channel 170 can be provided for introducing a make-up flow of liquid to the sample post-column, wherein the make-up flow normalizes the spray current. In various embodiments, there can be provided an electrospray ionization source 180 having one or more emitter nozzles 185 for receiving the make-up flow containing sample. In various aspects, a power supply 190 can be provided for providing a voltage to the one or more emitter nozzles and a measurement device 195 can be provided for measuring and monitoring the spray current of the one or more emitter nozzles.

As shown in FIGS. 3 to 7, in various embodiments, the liquid chromatography column can be micromachined on a first substrate. In various aspects, the make-up flow channel can be micromachined on a second substrate. In various embodiments, the system can further comprise a connector for connecting the first substrate to the second substrate.

In various embodiments, the make-up flow can be a dilute electrolyte. In various embodiments, the make-up flow can be a solvent without electrolyte. In various aspects, the make-up flow channel can comprise a tee junction, for example 175 in FIG. 2. In various embodiments, the make-up flow channel can comprise but is not limited to a y junction, concentric tubes, microfabricated channels, two arrays that are coupled, and a mixing tee junction on a substrate. In various embodiments, the one or more nozzles can comprise an array of emitters. In various aspects, the one or more nozzles can comprise a plurality of an array of emitters.

In various embodiments, the array of emitters or one or more of a plurality of an array of emitters can be replaced when the spray current exceeds the normalized spray current limits indicating nozzle failure.

In various aspects, the connector can comprise a transfer capillary. In various embodiments, the measurement device can comprise an ammeter.

In various embodiments, a positioning device can be provided for positioning the array of emitters or one or more of the plurality of the array of emitters.

In various aspects, the method further comprises providing a mass spectrometer for analyzing the spray from one or more emitter nozzles.

Figure 3:
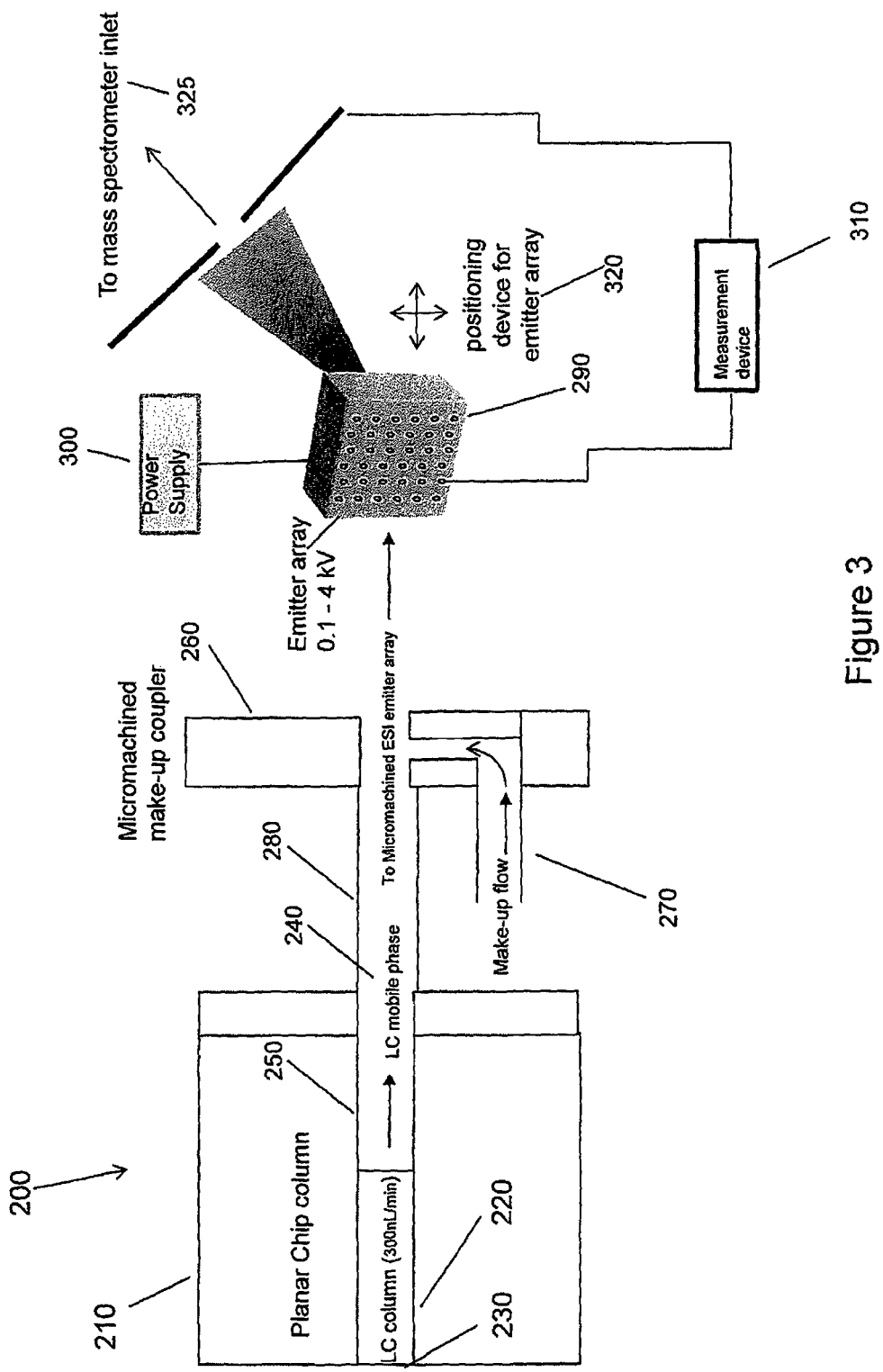
FIG. 3 is a schematic view of an electrospray system according to various embodiments of the applicant's teachings.

As shown in FIG. 3, and also in FIGS. 4 to 7, in various embodiments, the liquid chromatography column 220 can be micromachined on a first substrate. In various aspects, the make-up flow channel 270 can be micromachined on a second substrate. In various embodiments, the system can further comprise a connector 280 for connecting the first substrate 210 to the second substrate 260. FIG. 3 shows schematically, for example, an electrospray ion source system, generally indicated by reference number 200. The system 200 comprises a first substrate 210 having a liquid chromatography column 220 suitable for chromatographic separation of a sample. In various embodiments, a substrate can be any material that can be microfabricated or, including but not limited to dry etched, wet etched, laser etched, molded, or embossed, to have desired miniaturized surface features. In various aspects, the column 220 can have an inlet 230 for receiving the sample; an outlet 240 for ejecting the sample; and a channel 250 extending through the first substrate 210 between the inlet 230 and the outlet 240; a second substrate 260 having a make-up flow channel 270 for introducing a make-up flow of liquid to the sample post-column, wherein the make-up flow normalizes the spray current. In various embodiments, a connector 280 can be provided for connecting the first substrate 110 to a second substrate 160. In various aspects, one or more electrospray ionization emitter nozzles 290 can receive the make-up flow containing sample, and a power supply 300 can provide a voltage to the one or more emitter nozzles 290. In various aspects, a measurement device 310 can measure and monitor the spray current of the one or more emitter nozzles 290.

In various embodiments, as shown in FIGS. 1 and 2 the electrospray system need not be micromachined and instead can be a typical electrospray system incorporating the applicant's teachings of introducing make-up flow for normalizing the spray current. In various aspects, the make-up flow can be introduced via a tee junction as shown, for example, as 175 in FIG. 2. In various embodiments, the make-up flow channel can comprise but is not limited to a y junction, concentric tubes, microfabricated channels, two arrays that are coupled, and a mixing tee junction on a substrate.

In various embodiments, the make-up flow can be a dilute electrolyte, and in various aspects, the make-up flow can be a solvent without electrolyte.

In various aspects, the one or more nozzles can comprise an array of emitters, and in various embodiments, the one or more nozzles can comprise a plurality of an array of emitters.

In various embodiments, the array of emitters or one or more of the plurality of the array of emitters can be replaced when the spray current exceeds the normalized spray current limits indicating nozzle failure.

In various aspects, the connector can comprise a transfer capillary, and the measurement device can comprise an ammeter.

In various embodiments, the system can further comprise a positioning device 320 for positioning the array of emitters or one or more of the plurality of the array of emitters. In various embodiments, the positioning device can comprise stepper motors or any other suitable device to position the one or more array of emitters. In various aspects, the system can further comprise a mass spectrometer for analyzing the spray from one or more emitter nozzles.

In various embodiments, the system can comprise, for example, a nanospray, a Turbo V™ source, or any other suitable electrospray ion source.

In various embodiments, a method is provided for detecting emitter failure comprising providing a first substrate 210 having a micromachined liquid chromatography column 220 suitable for chromatographic separation of a sample; the column 220 having an inlet 230 for receiving the sample; an outlet 240 for ejecting the sample; and a channel 250 extending through the first substrate 210 between the inlet 230 and the outlet 240. In various embodiments, the method comprises providing a second substrate 260 having a make-up flow channel 270 for introducing a make-up flow of liquid to the sample post-column, wherein the make-up flow normalizes the spray current. In various aspects, a connector 280 can be provided for connecting the first substrate 210 to the second substrate 260. In various embodiments, one or more micromachined electrospray ionization emitter nozzles 290 can be provided for receiving the make-up flow containing sample. In various aspects, a power supply 300 can provide a voltage to the one or more emitter nozzles, and a measurement device 310 can be provided to measure and monitor the spray current of the one or more emitter nozzles.

In various embodiments, the electrospray system in the method need not be micromachined and instead can be a typical electrospray system incorporating the applicant's teachings of introducing make-up flow for normalizing the spray current. In various aspects, the make-up flow can be introduced via a tee junction as shown, for example, as 175 in FIG. 2. In various embodiments, the make-up flow channel can comprise but is not limited to a y junction, concentric tubes, microfabricated channels, two arrays that are coupled, and a mixing tee junction on a substrate.

In various embodiments, the make-up flow can be a dilute electrolyte. The dilute electrolyte can be an acidic or basic species. In various aspects, the make-up flow can be a solvent without electrolyte, such as a protic or aprotic solvent.

In various embodiments, the one or more nozzles can comprise an array of emitters, and in various embodiments, the one or more nozzles can comprise a plurality of an array of emitters.

In various embodiments, the array of emitters or one or more of the plurality of the array of emitters can be replaced when the spray current exceeds the normalized spray current limits indicating nozzle failure.

In various aspects, the connector can comprise, for example, a transfer capillary, and the measurement device can comprise, for example, an ammeter.

In various embodiments, the method can further comprise a positioning device, including but not limited to, stepper motors for positioning the array of emitters or one or more of the plurality of the array of emitters. In various aspects, the method can further comprise providing a mass spectrometer for analyzing the spray from one or more emitter nozzles.

Figure 4:
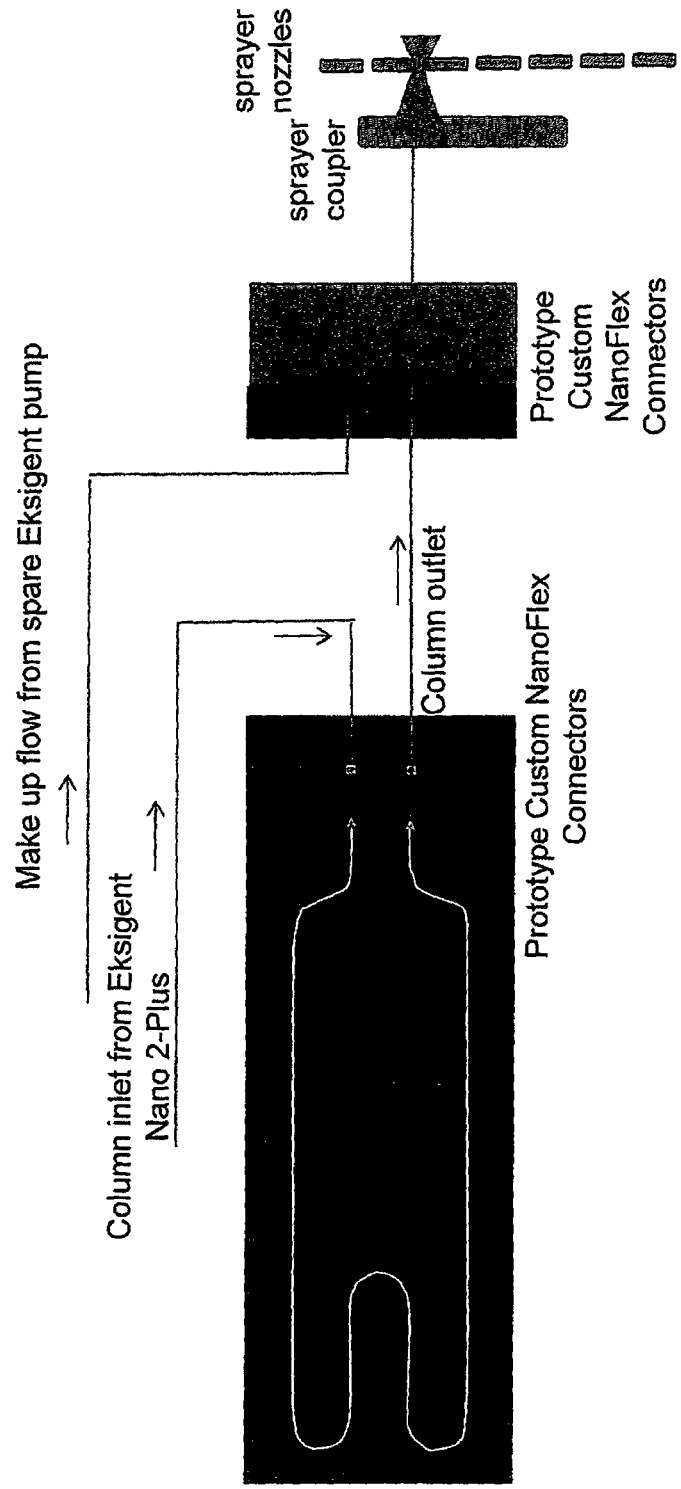
FIG. 4 is a schematic view of an electrospray system according to various embodiments of the applicant's teachings.
Figure 5:
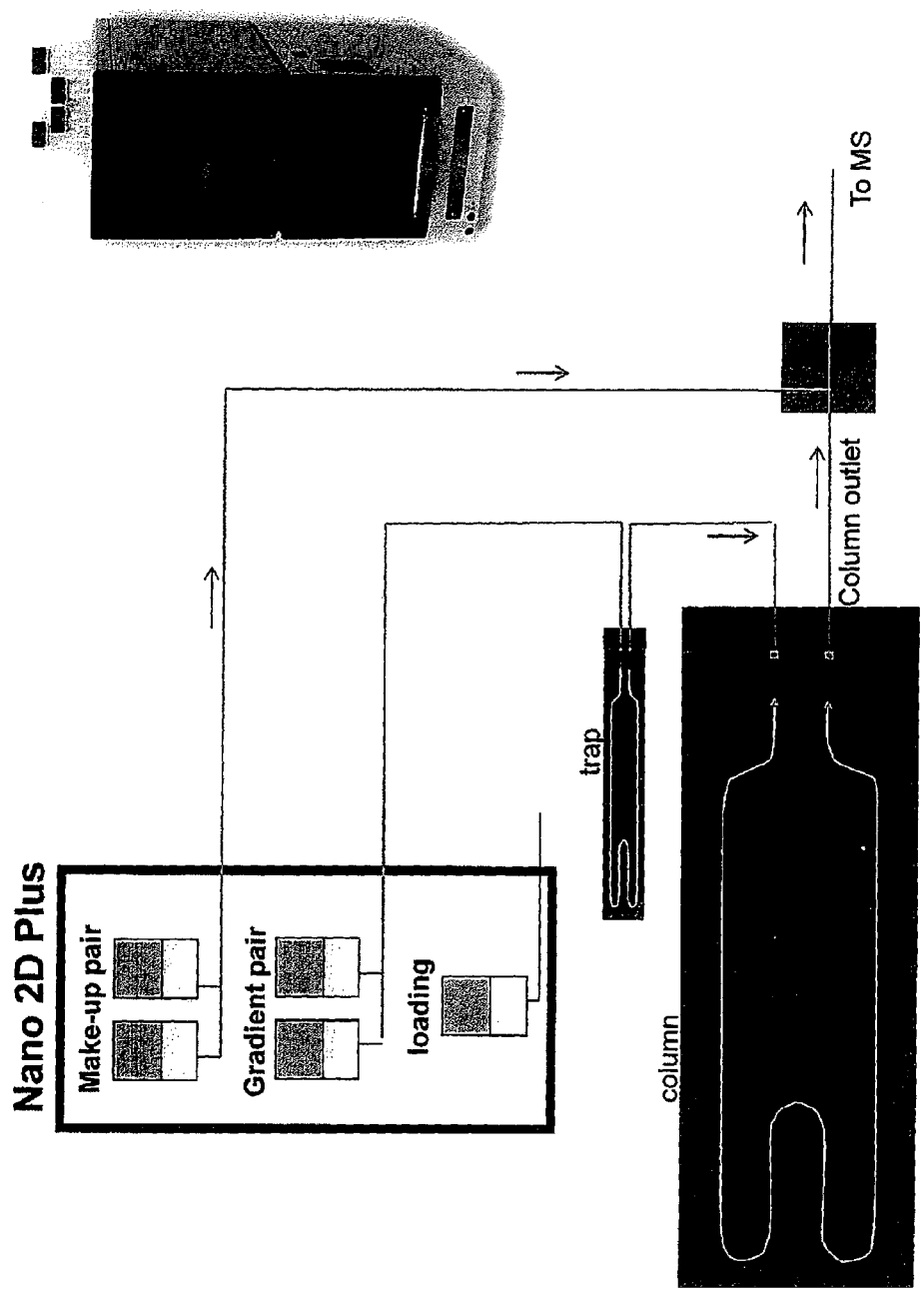
FIG. 5 is a schematic view of an electrospray system according to various embodiments of the applicant's teachings.

In various embodiments, the method can comprise providing, for example, a nanospray, a Turbo V™ source, or any other suitable electrospray ion source. FIGS. 3, 4, and 5 show a micromachined nanospray system, according to various embodiments of the applicant's teachings. In various aspects, the make-up flow is pumped post-column into the sample flow.

Figure 6:
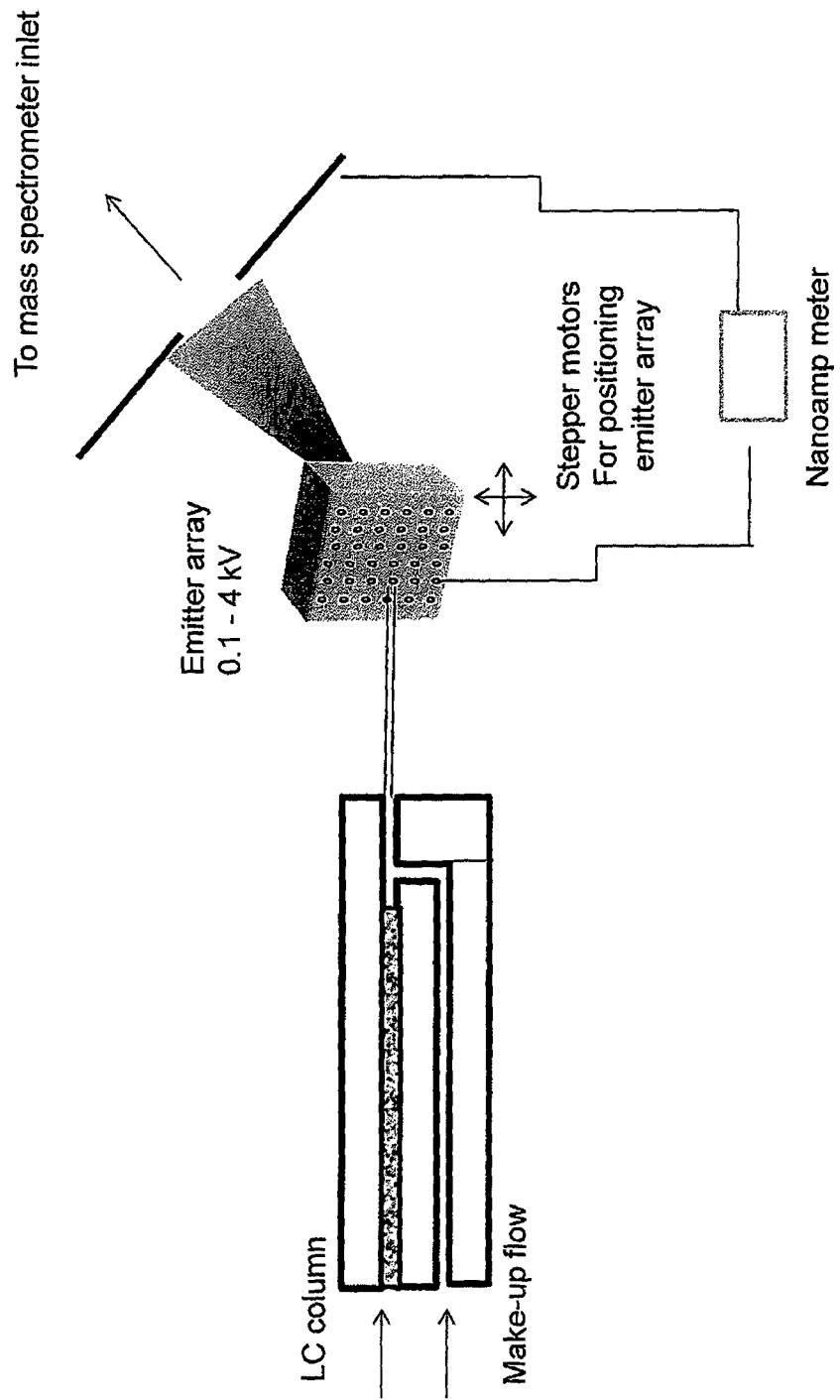
FIG. 6 is a schematic view of an electrospray system according to various embodiments of the applicant's teachings.
Figure 7:
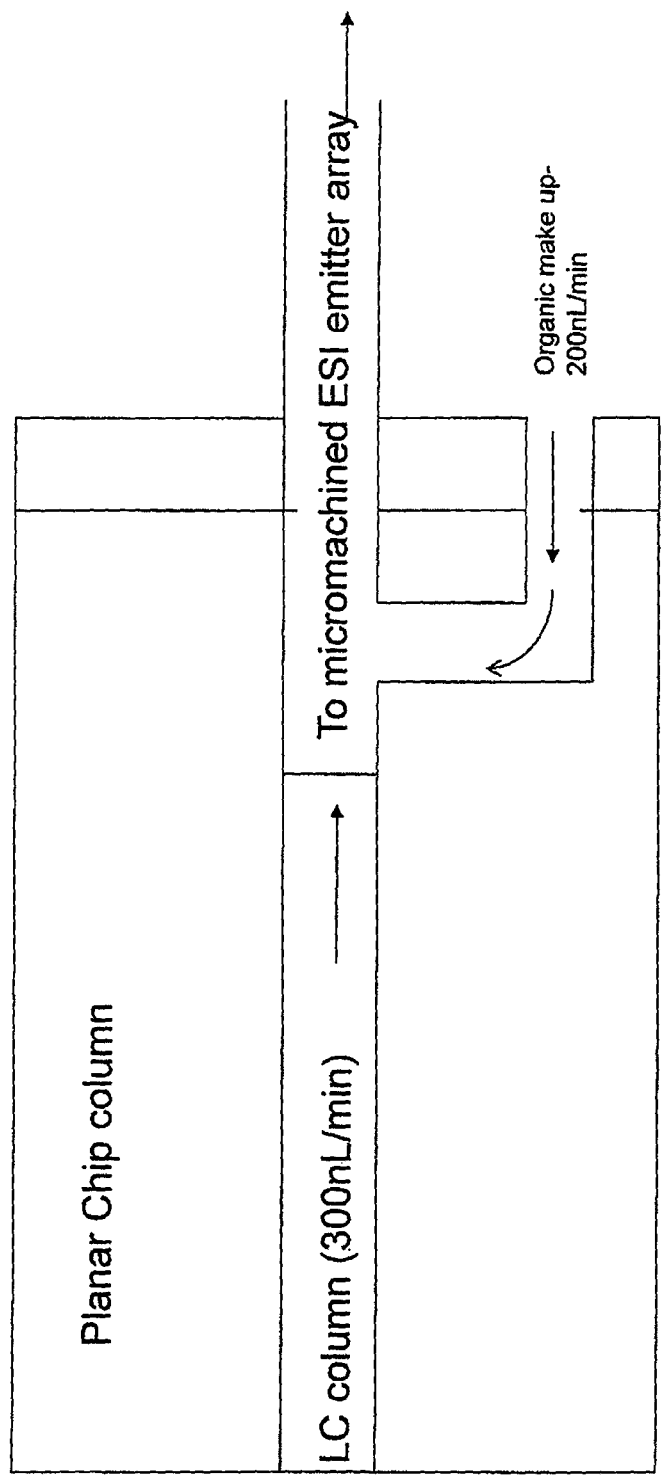
FIG. 7 is a schematic view of an electrospray system according to various embodiments of the applicant's teachings.

FIGS. 6 and 7 show an integrated electrospray system in which a make-up flow channel providing make-up flow is on the first substrate.

Figure 8:
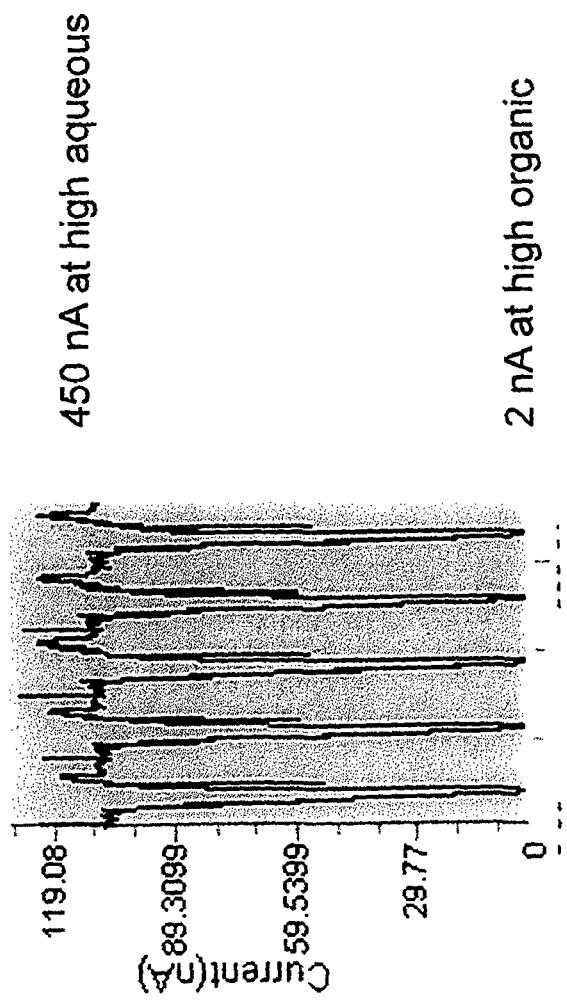
FIG. 8 shows the broad range of spray current measurements within a single sample.
Figure 9:
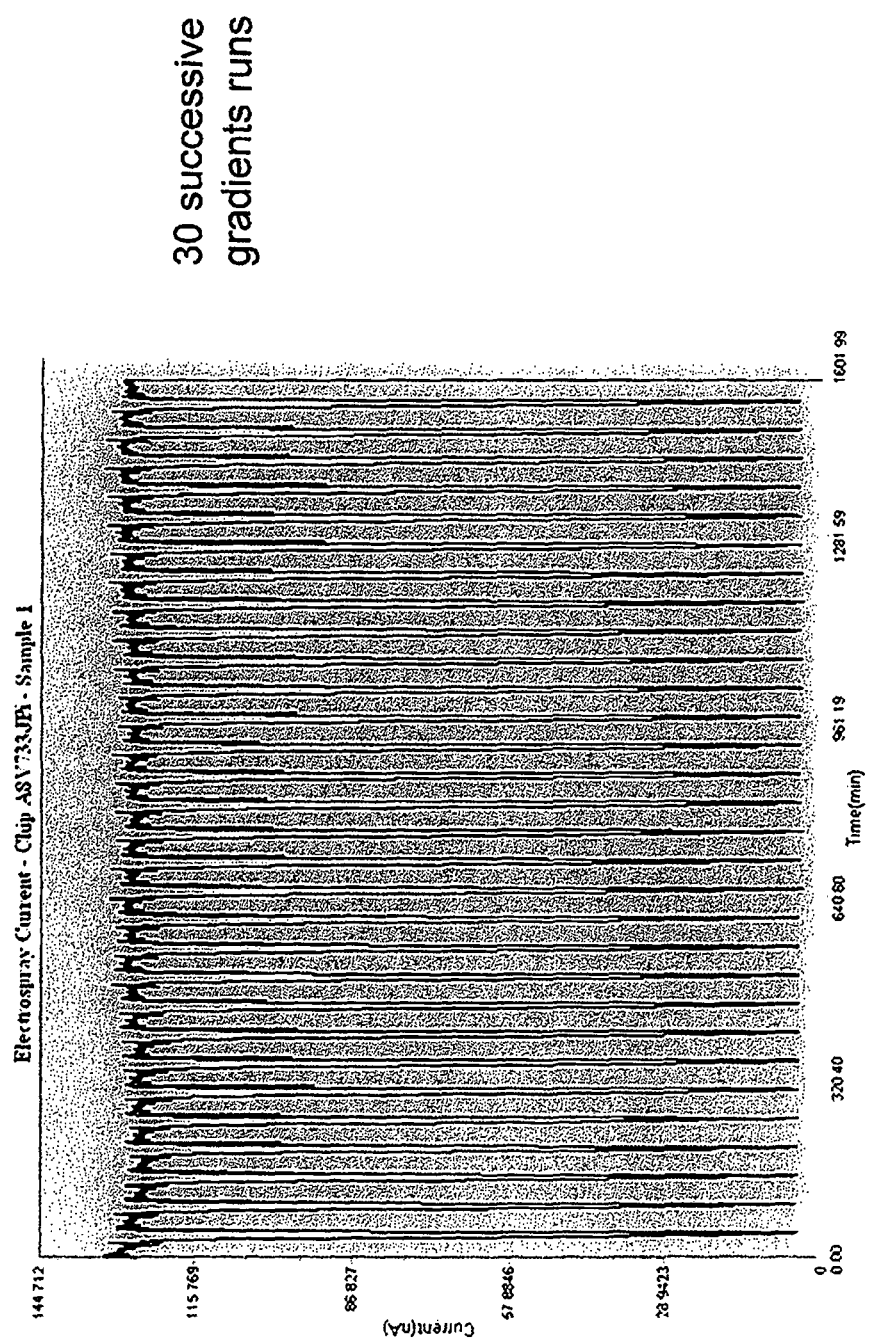
FIG. 9 shows the broad range of spray current measurements in 30 successive runs.

FIG. 8 shows five LC gradient runs each covering a solvent composition range of 100% aqueous (0.1% formic acid) to 100% organic (acetonitrile). The broad range of spray current measurements within a single sample can make it difficult to detect nozzle failure. FIG. 9 shows 30 successive gradient runs with a broad range of spray current measurements. Nozzles most commonly fail during high aqueous portion of gradient. Under these conditions, the measured spray current drops around 35 nA, as shown in FIG. 8, which is not sufficient to detect emitter failure and trigger an emitter replacement. Without the use of make-up flow the spray current values swing to extreme values during an LC gradient run making the use of spray current detection as a diagnostic tool for detecting spray failure ineffective. For example, a range spanning from 1 nA to 150 nA is typical from the beginning of a gradient to the end of the gradient with additional spikes in between during regions of bulk biological matrix elution.

Figure 10:
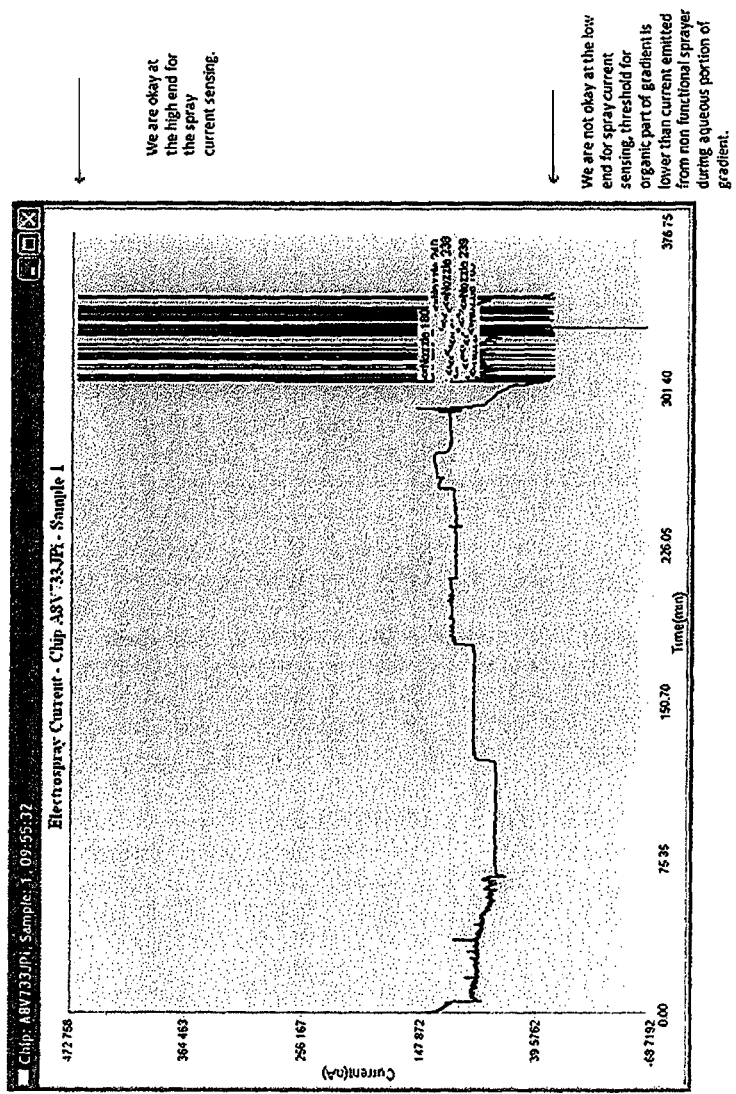
FIG. 10 shows that nozzles most commonly fail during high aqueous portion of gradient.

FIG. 10 shows analytical gradient for negative ion mode precursor ion scanning experiments and shows that the presence of the make-up flow can enable stable and reproducible negative ion mode nano-LC/MS with full analytical gradients. With the use of make-up flow post column, the spray current can be normalized within a narrow range during a gradient run so that emitter failure can be readily detected when spray current falls outside the normalized range.

The following illustrates an experimental example of incorporating make-up flow post column in an electrospray system.

Sample Preparation:

All samples were diluted in water with 0.1% formic acid. Samples included protein digests comprising BSA and α-casein. In addition, a 68 compound small molecule mixture was prepared for positive ion mode analysis and an 8 compound mixture was prepared for negative ion mode, comprising aztreonam, digoxin, estradiol sulfate, fluorescein, furosemide, ibuprofen, naproxen, and taurocholic acid.

HPLC Conditions:

An Eksigent Nanoflex column (5 cm long, 75 um I.D. 3 um particle size) was used with post-column make-up flow addition. Nano-LC experiments were conducted with an Eksigent nano 2D Plus (Livermore, Calif.). Gradients were run out from 98% acidified water to 20% acidified water over either 42 or 8 minutes. Injection volumes were 1 uL and the LC flow rate was 400 nL/min throughout. A make-up flow of 200 nL/min acetonitrile with 0.1% formic acid was maintained throughout such that the spray solvent never exceeded 67% aqueous content.

MS Conditions:

A 5500 QTRAP® mass spectrometer system was used operating in multiple reaction monitoring (MRM) mode.

Figure 11:
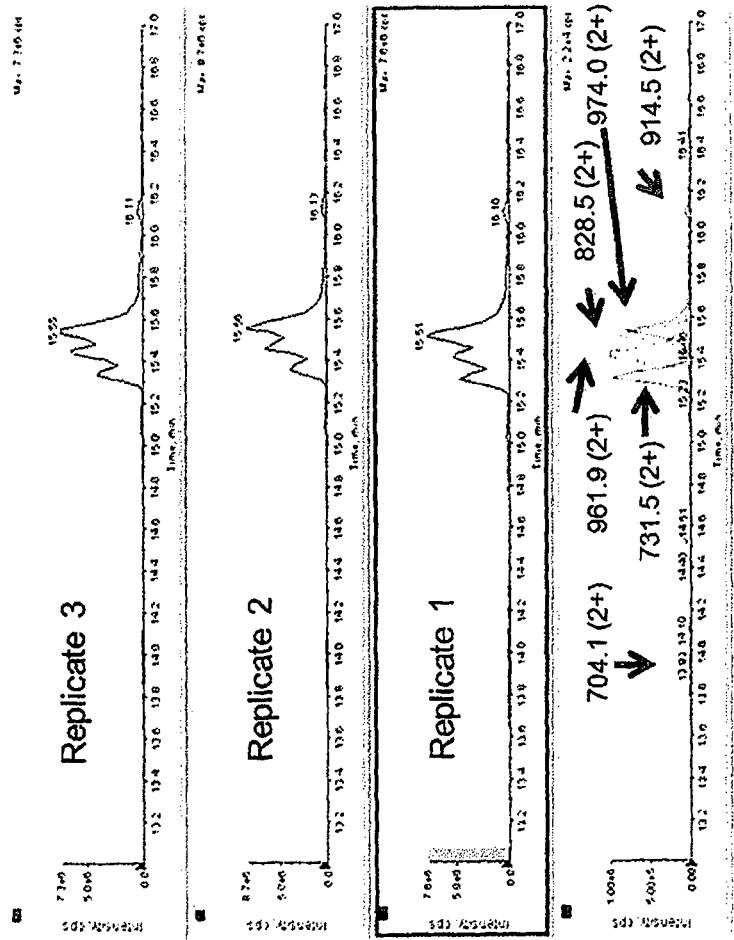
FIG. 11 shows an example according to various embodiments of the applicant's teachings.

FIG. 11 shows triplicate precursor ion scanning experiments monitoring parents of m/z −79 for the presence of phosphopeptides. The analytical gradient for negative ion mode precursor ion scanning experiments is presented in FIG. 12. The presence of the make-up flow enabled stable and reproducible negative ion mode nano-LC/MS with full analytical gradients.

In various embodiments, a differential mobility spectrometry (DMS) coupled to mass spectrometry can be used to separate ions in the gas-phase. The DMS can be capable of separating ions that are isomers of one another, be they structural isomers, stereoisomers, or even isotopologs. In various embodiments of the applicant's teachings, another capability of DMS is presented in the separation of two closely related ions that differ only by the site of protonation.

Figure 13:
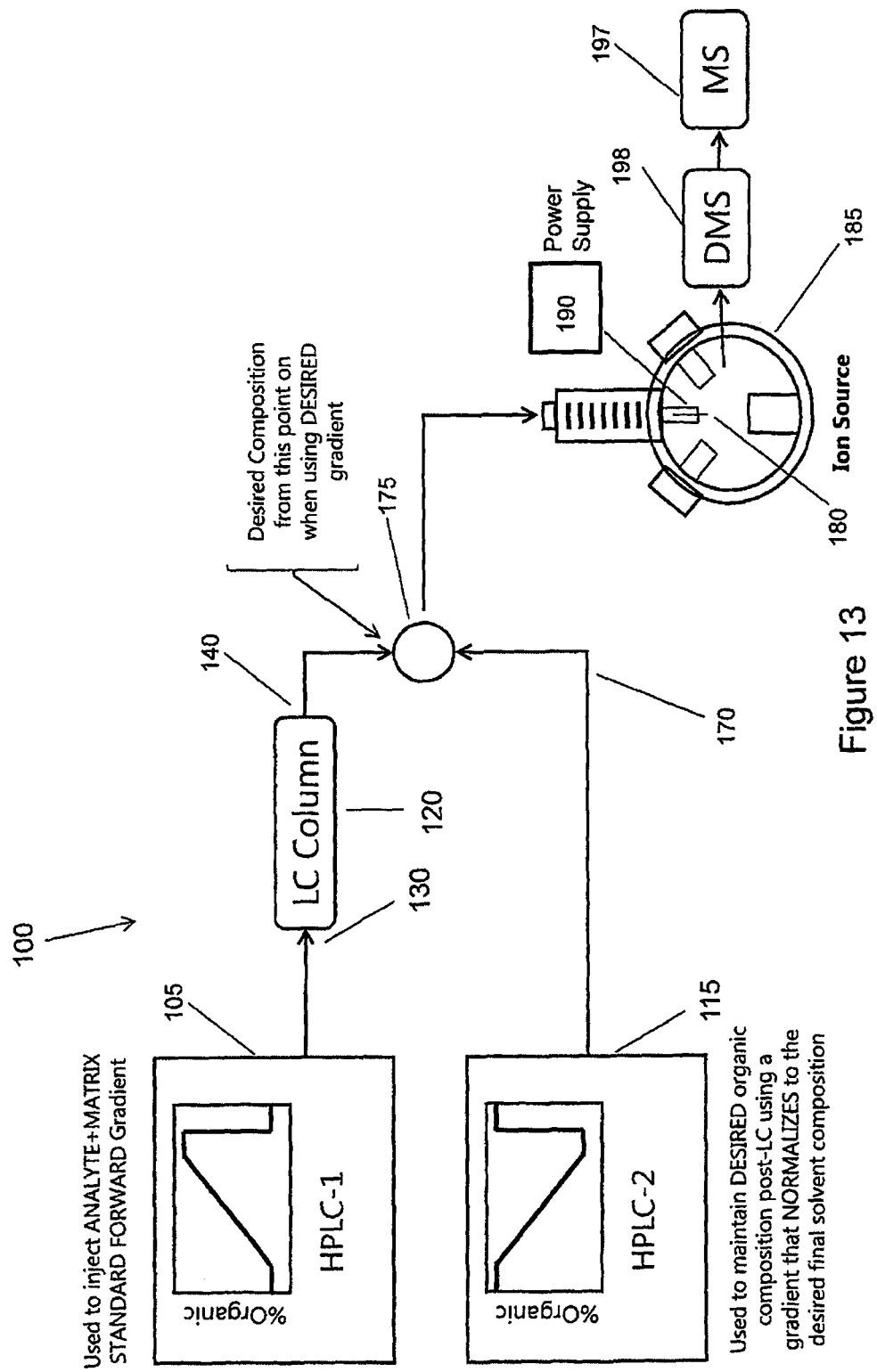
FIG. 13 shows a schematic of an electrospray system in conjunction with a differential mobility spectrometer (DMS) according to various embodiments of the applicant's teachings.
Figure 14:
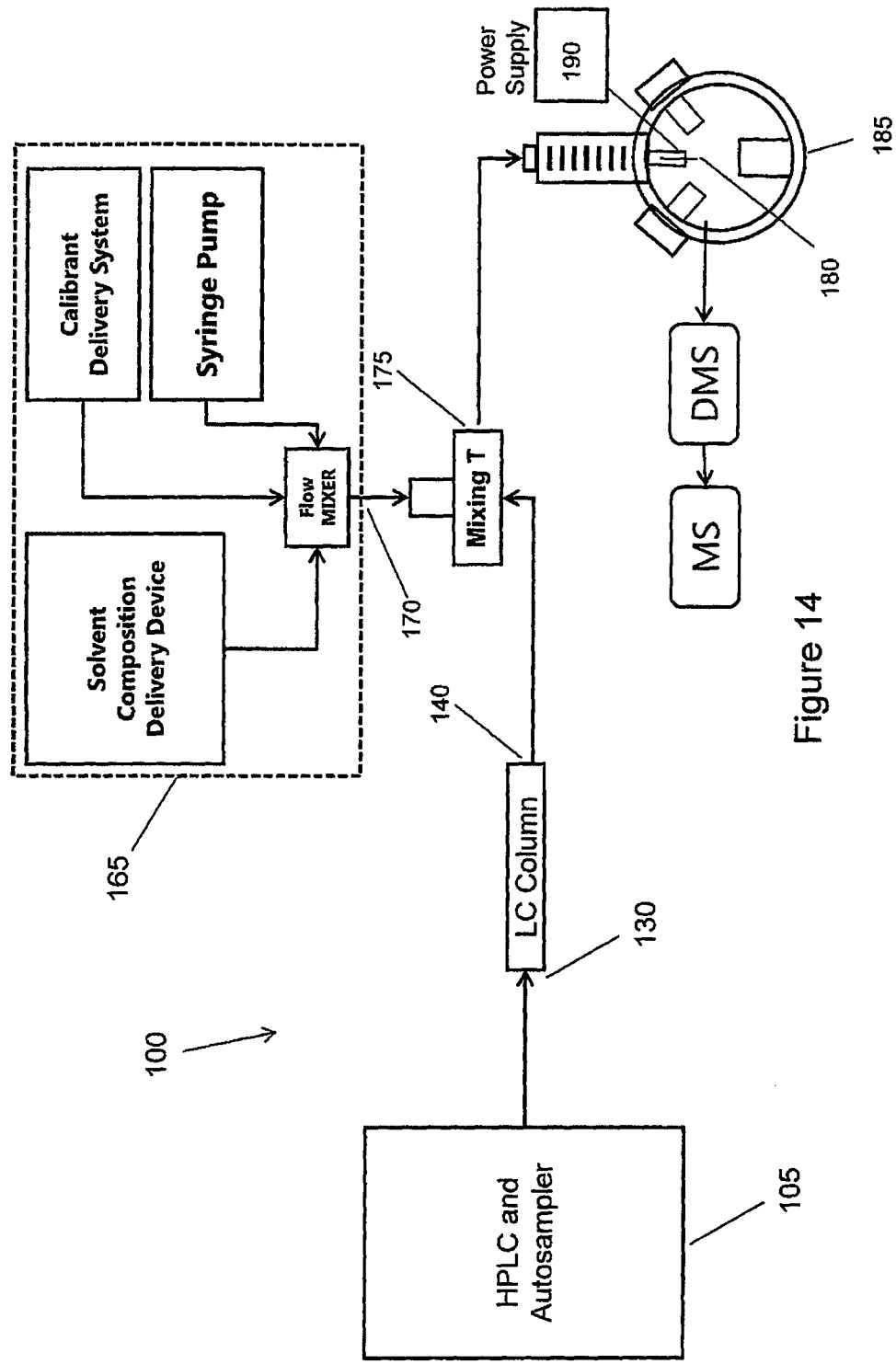
FIG. 14 shows a schematic of an electrospray system in conjunction with a DMS according to various embodiments of the applicant's teachings.

A method and system for altering the site of protonation is provided. Reference is made to FIGS. 13 and 14 which show schematically, for example, an electrospray ion source system, generally indicated by reference number 100. As known in the art, an HPLC pump 105 can move mobile phase and sample through a liquid chromatography column 120. The system 100 comprises a liquid chromatography column 120 suitable for chromatographic separation of a sample. In various aspects, the column 120 can have an inlet 130 for receiving the sample and an outlet 140 for ejecting the sample. In various embodiments, the system can comprise a make-up flow channel 170 for introducing a make-up flow of liquid to the sample post-column, indicated at 175, wherein the make-up flow normalizes the spray current. In various embodiments, an HPLC pump 115, shown in FIG. 13, can be used to maintain the desired organic composition post-LC. In various embodiments, delivery systems can be used to deliver the make-up flow to the sample post-column, as shown in FIG. 14. In various aspects, an electrospray ionization source 180 can be provided having one or more emitter nozzles 185 for receiving the make-up flow containing sample. In various embodiments, the system can comprise, for example, a nanospray, a Turbo V™ source, or any other suitable electrospray ion source.

In various embodiments, there can comprise a power supply 190 for providing a voltage to the one or more emitter nozzles. In various embodiments, an ion mobility device, including but not limited to low field mobility, DMA, etc., can be provided for separating the ions. In various embodiments, a differential ion mobility spectrometer can be provided for separating the ions.

Figure 15:
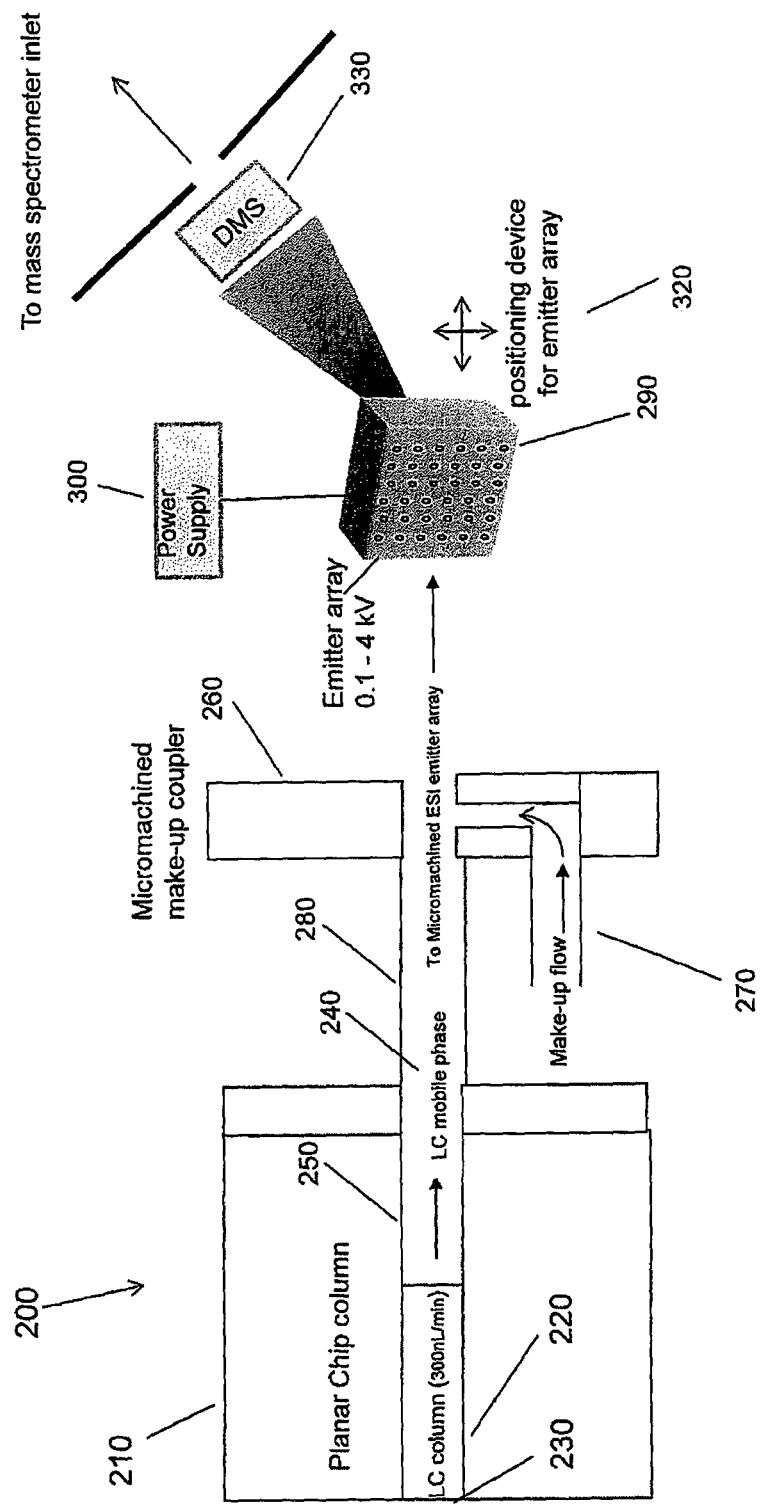
FIG. 15 shows a schematic of an electrospray system in conjunction with a DMS according to various embodiments of the applicant's teachings.

As shown in FIG. 15, in various embodiments, the liquid chromatography column can be micromachined on a first substrate 210. In various aspects, the make-up flow channel 270 can be micromachined on a second substrate 260. In various embodiments, the system can further comprise a connector 280 for connecting the first substrate 210 to the second substrate 260. In various aspects, the connector can comprise a transfer capillary.

In various embodiments, the make-up flow can be a dilute electrolyte. In various aspects, the make-up flow can be a solvent without electrolyte. In various embodiments, the make-up flow channel can comprise a tee junction. In various embodiments, the make-up flow channel can comprise but is not limited to a y junction, concentric tubes, microfabricated channels, two arrays that are coupled, and a mixing tee junction on a substrate.

In various embodiments, the one or more nozzles can comprise an array of emitters. In various aspects, the one or more nozzles can comprise a plurality of an array of emitters.

In various embodiments, the array of emitters or one or more of the plurality of the array of emitters can be replaced when the spray current exceeds the normalized spray current limits indicating nozzle failure.

In various embodiments, there can be provided a positioning device for positioning the array of emitters or one or more of the plurality of the array of emitters.

In various aspects, the system can comprise a mass spectrometer 197 for analyzing the spray from one or more emitter nozzles.

In various embodiments, a method is provided for detecting emitter failure comprising providing liquid chromatography column 120 suitable for chromatographic separation of a sample. In various aspects, the column 120 can have an inlet 130 for receiving the sample and an outlet 140 for ejecting the sample. In various embodiments, a make-up flow channel 170 can be provided for introducing a make-up flow of liquid to the sample post-column, wherein the make-up flow normalizes the spray current. In various embodiments, there can be provided an electrospray ionization source 180 having one or more emitter nozzles 185 for receiving the make-up flow containing sample. In various aspects, a power supply 190 can be provided for providing a voltage to the one or more emitter nozzles. In various embodiments, an ion mobility device, including but not limited to low field mobility, DMA, etc., can be provided for separating the ions. In various embodiments, a differential ion mobility spectrometer can be provided for separating the ions.

As shown in FIG. 15, in various embodiments, the liquid chromatography column can be micromachined on a first substrate. In various aspects, the make-up flow channel can be micromachined on a second substrate. In various embodiments, the system can further comprise a connector for connecting the first substrate to the second substrate.

In various embodiments, the make-up flow can be a dilute electrolyte. In various embodiments, the make-up flow can be a solvent without electrolyte. In various aspects, the make-up flow channel can comprise a tee junction as shown, for example, as 175 in FIG. 14. In various embodiments, the make-up flow channel can comprise but is not limited to a y junction, concentric tubes, microfabricated channels, two arrays that are coupled, and a mixing tee junction on a substrate. In various embodiments, the one or more nozzles can comprise an array of emitters. In various aspects, the one or more nozzles can comprise a plurality of an array of emitters.

In various embodiments, the array of emitters or one or more of a plurality of an array of emitters can be replaced when the spray current exceeds the normalized spray current limits indicating nozzle failure.

In various aspects, the connector can comprise a transfer capillary. In various embodiments, a positioning device can be provided for positioning the array of emitters or one or more of the plurality of the array of emitters.

In various aspects, the method further comprises providing a mass spectrometer for analyzing the spray from one or more emitter nozzles.

Reference is made to FIG. 15 in which in various embodiments, a micromachined electrospray ion source system 200 is provided for altering the site of protonation of ions. In various aspects, the system 200 can comprise a first substrate 210 having a micromachined liquid chromatography column 220 suitable for chromatographic separation of a sample; the column 220 having an inlet 230 for receiving the sample; an outlet 240 for ejecting the sample; and a channel 250 extending through the first substrate 210 between the inlet 230 and the outlet 240. In various embodiments, a substrate can be any material that can be microfabricated or micromachined, including but not limited to dry etched, wet etched, laser etched, molded, or embossed, to have desired miniaturized surface features. In various aspects, the system 200 can comprise a second substrate 260 having a make-up flow channel 270 for introducing a make-up flow of liquid to the sample post-column, wherein the make-up flow alters the site of protonation of ions. In various aspects, the make-up flow alters the site of charging of ions. In various aspects, an electrospray ion source system is provided for altering the site of charging of ions. One skilled in the art can appreciate that one can alter the site of charging a molecule in a number of ways including but not limited to changing the site of protonation, changing the site of deprotonation, changing the site of a positive adduct ion, changing the site of a negative adduct ion, changing the site of a radical cation (conventional or distonic), changing the site of a radical anion (conventional or distonic), or other forms of charging as known in the art. In various embodiments, a connector 280 can connect the first substrate 210 to the second substrate 260, and one or more micromachined electrospray ionization emitter nozzles 290 can receive the make-up flow containing sample. In various aspects, a power supply 300 can provide a voltage to the one or more emitter nozzles. In various embodiments, an ion mobility device, including but not limited to low field mobility, DMA, etc., can be provided for separating the ions. In various embodiments, a differential ion mobility spectrometer 330 can be provided to separate the ions.

In various embodiments, the electrospray system need not be micromachined and instead can be a typical electrospray system in conjunction with a DMS as shown in FIGS. 13 and 14 incorporating the applicant's teachings of introducing make-up flow for altering the protonation site of ions. In various aspects, the make-up flow can be introduced via a tee junction 175 as shown in FIG. 14. In various embodiments, the make-up flow channel can comprise but is not limited to a y junction, concentric tubes, microfabricated channels, two arrays that are coupled, and a mixing tee junction on a substrate.

In various aspects, the make-up flow can comprise acetonitrile, methanol or any other suitable make-up flow, including mixtures.

In various embodiments, the one or more nozzles can comprise an array of emitters, and in various aspects, the one or more nozzles can comprise a plurality of an array of emitters.

In various aspects, the connector can comprise a transfer capillary. In various embodiments, the system can further comprise a positioning device 320 for positioning the array of emitters or one or more of the plurality of the array of emitters. In various aspects, the positioning device can comprise stepper motors or any other device suitable for positioning the array of emitters.

In various embodiments, the system can further comprise a mass spectrometer for analyzing the ions from the differential mass spectrometer.

In various aspects, a method is provided for altering the site of protonation of ions comprising providing a first substrate 210 having a micromachined liquid chromatography column 220 suitable for chromatographic separation of a sample; the column 220 having an inlet 230 for receiving the sample; an outlet 240 for ejecting the sample; and a channel 250 extending through the substrate between the inlet 230 and the outlet 240. In various embodiments, the method can provide a second substrate 260 having a make-up flow channel 270 for introducing a make-up flow of liquid to the sample post-column, wherein the make-up flow alters the site of protonation of ions. In various aspects, the make-up flow alters the site of charging of ions. In various aspects, one skilled in the art can appreciate that one can alter the site of charging a molecule in a number of ways including but not limited to changing the site of protonation, changing the site of deprotonation, changing the site of a positive adduct ion, changing the site of a negative adduct ion, changing the site of a radical cation (conventional or distonic), changing the site of a radical anion (conventional or distonic), or other forms of charging as known in the art. In various aspects, a connector 280 can be provided for connecting the first substrate 210 to the second substrate 260, and one or more micromachined electrospray ionization emitter nozzles 290 can be provided for receiving the make-up flow containing sample. In various aspects, a power supply 300 can provide a voltage to the one or more emitter nozzles, and in various embodiments, a differential mobility spectrometer 330 can be provided for separating the ions. In various embodiments, an ion mobility device, including but not limited to low field mobility, DMA, etc., can be provided for separating the ions.

In various embodiments, the electrospray in the method need not be micromachined and instead can be a typical electrospray system, as shown for example in FIGS. 13 and 14, incorporating the applicant's teachings of introducing make-up flow for altering the protonation site of ions. In various aspects, the make-up flow can be introduced via a tee junction 175 as shown in FIG. 14. In various embodiments, the make-up flow channel can comprise but is not limited to a y junction, concentric tubes, microfabricated channels, two arrays that are coupled, and a mixing tee junction on a substrate.

In various aspects, the make-up flow can comprise any suitable aprotic solvent as known in the art, such as, for example, acetonitrile, and in various aspects, the make-up flow can comprise any suitable protic solvent as known in the art, such as, for example, methanol.

In various embodiments, the one or more nozzles can comprise an array of emitters, and in various aspects, the one or more nozzles can comprise a plurality of an array of emitters.

In various aspects, the connector can comprise a transfer capillary. In various embodiments, the method can further comprise providing a positioning device for positioning the array of emitters or one or more of the plurality of the array of emitters.

In various embodiments, the method can further comprise providing a mass spectrometer for analyzing the ions from the differential mass spectrometer.

Figure 17:
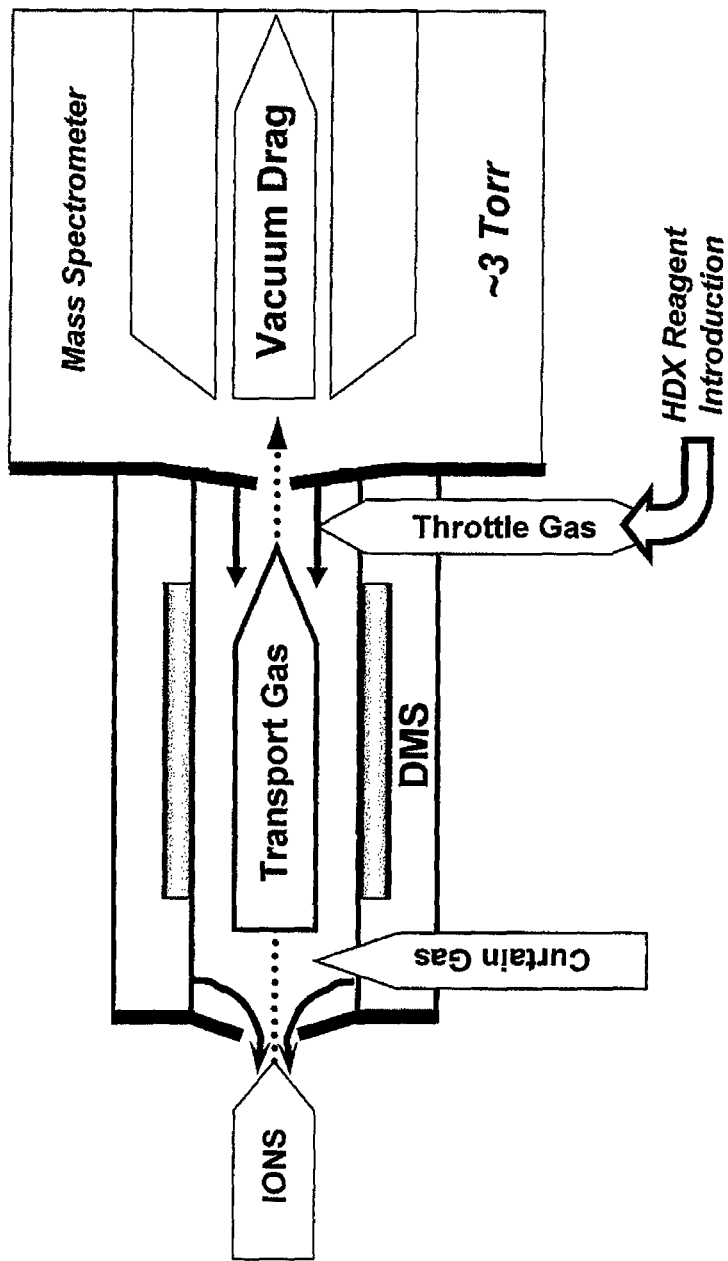
FIG. 17 shows a cross-sectional view of the DMS depicting the relevant components and gas flows.

Reference is made to FIG. 17 which shows a cross-sectional view of a DMS system depicting the relevant components and gas flows.

Figure 18:
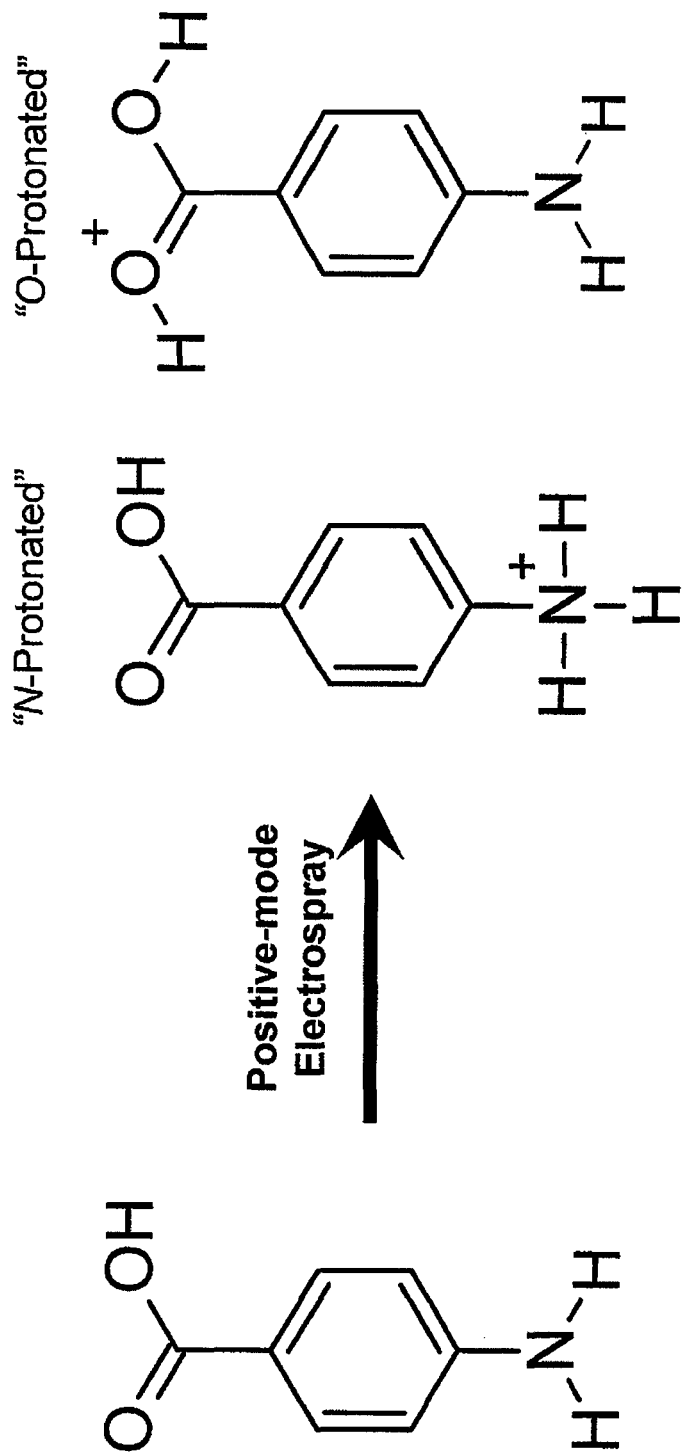
FIG. 18 shows the structures of the two most energetically favored sites of protonation for 4-aminobenzoic acid.

Reference is made to FIG. 18 which shows, as an example, the structures of the two most energetically favored sites of protonation for 4-aminobenzoic acid formed by positive-mode electrospray ionization.

For example, protonated 4-aminobenzoic acid molecules generated by electrospray ionization (ES) can exist with the proton residing either on the amine nitrogen (N-protonated) or the carboxylic acid oxygen (O-protonated). These two discrete ion populations can be generated as intractable mixtures that cannot be separated based upon mass analysis alone. However, in accordance with the applicant's teachings, the two ions can be discriminated and separated with the use of make-up flow in conjunction with a DMS.

For example, in accordance with the applicant's teachings, the N- and the O-protonated 4-aminobenzoic acid molecules can be identified and separated. An example of DMS-based separation of the same protonated molecules differing only in their sites of protonation is provided below. Support for the proposed sites of protonation can be provided by the observed influence of ESI solvent ion ratios, distinguishable MS/MS fragmentation for each DMS-separated isomer, different HDX behaviour for each species, and the different fundamental ion mobility behaviours for the two ion types to the DMS itself.

Experimental Example

Materials. All three isomers of aminobenzoic acid (2-, 3-, and 4-aminobenzoic acid) and deuterated water (100%) were obtained from Sigma-Aldrich (St. Louis, Mo.) and were used without further purification. HPLC-grade acetonitrile was purchased from Caledon Laboratory Chemicals (Georgetown, ON), and HPLC-grade methanol was purchased from J.T. Baker (Avantor Performance Chemicals, Center Valley, Pa.); these solvents were also used without further purification. Distilled deionized water (15 MΩ) was produced in-house using a Millipore (Billerica, Mass.) Integral 10 water purification system.

Figure 16:
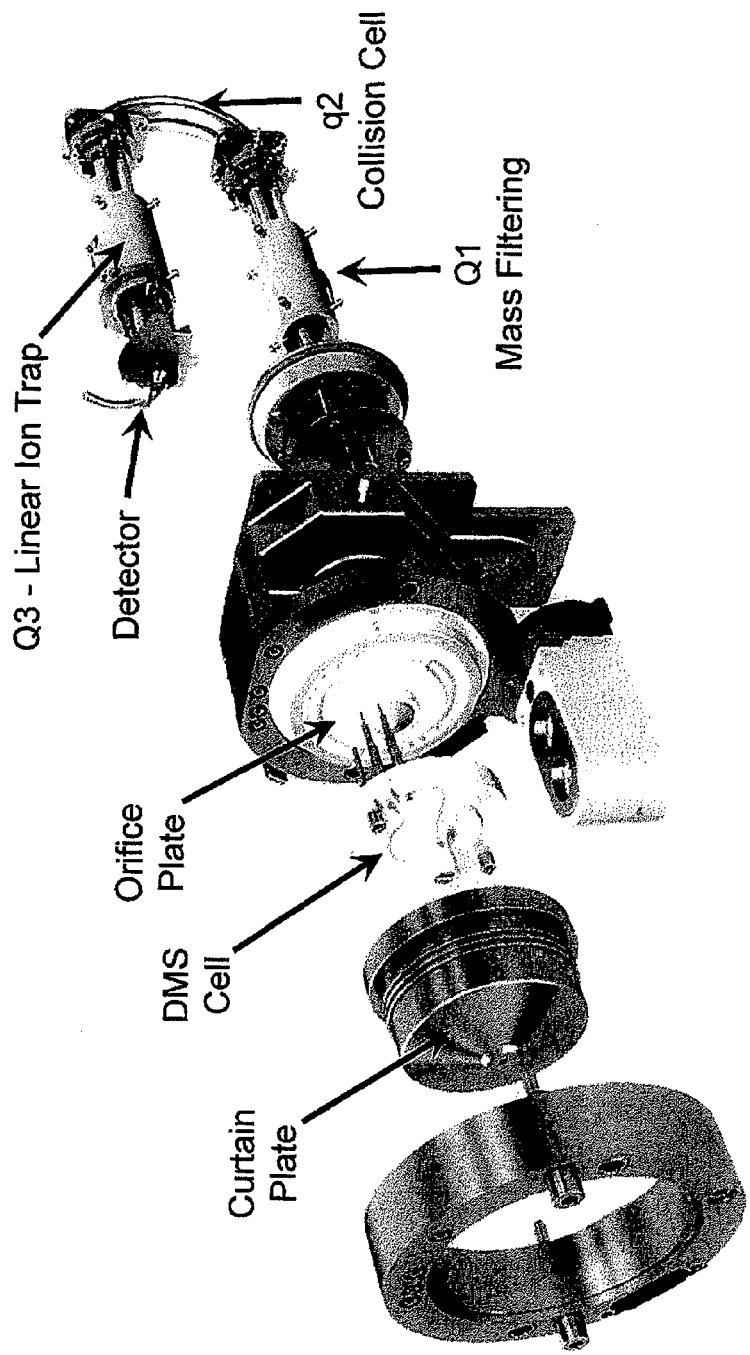
FIG. 16 shows an exploded view of a DMS coupled to a mass spectrometer.

Differential Ion Mobility—Mass Spectrometry. A differential mobility spectrometer (SelexION™ Technology, AB Sciex, Concord, ON) system as shown in FIGS. 16 and 17 was mounted on a 5500 QTRAP® system (AB Sciex), between a TurboV™ ESI source and the mass spectrometer's sampling orifice. The ESI probe was maintained at a voltage of 4800 V, with a source temperature of 150° C., nebulizing gas flow of 30 psi, and auxiliary gas flow of 20 psi. The DMS cell was maintained at 150° C., and nitrogen was used as the curtain gas (3.5 L/min), throttle gas (0 or 0.7 L/min), and target gas (~3 mTorr) for the MS/MS experiments. In all experiments, a 4-ABA solution (10 ng/mL) was infused into the ESI probe at a rate of 20 μL/min using a syringe pump. This system also contains a tee with which the analyte solution can be mixed with an added solvent system.

The DMS cell consists of two parallel planar electrodes (30×10 mm) separated by a 1-mm gap. Ions generated by the ESI source are carried by the transport gas into this cell while an asymmetric RF waveform (3 MHz) is applied in the transverse direction to the gas flow to the two electrodes. This is termed the Separation Voltage (SV), ranging in amplitude from 0 to 4000 $V_P$ and providing fields from 0-132 Td (Townsend, 1 Td=$10^{-17}$ V cm$^{-2}$). The SV causes ions to oscillate rapidly toward one electrode or the other, depending upon the mobility behavior of the ion. To counterbalance this force, a second DC potential is also applied to the electrodes and is termed the Compensation Voltage (CV); the CV serves to deflect ions from collisions with the electrode surface and can be used to steer ions on stable trajectories for successful passage through the DMS cell.

For the DMS experiments conducted in this study, one of two DMS operational modes was employed. In the first mode, the SV was held at an optimum value (+3500 V) while the CV was scanned from −15V to +15V in 0.1-V increments; at each incremental value of CV, an MS or MS/MS spectrum of protonated 4-ABA was recorded (vide infra). Data from this operational mode is plotted in the form of an ionogram. For the second mode of operation, both the SV and CV are scanned synchronously. For example, as SV is stepped from 0 to 3500V (in 500-V increments), CV is scanned from −15V to +15V at each incremental SV value; again, at each 0.1-V increment of CV, an MS/MS spectrum of protonated 4-ABA was recorded. Data from this second DMS operation mode are plotted as dispersion plots, with SV as the y-axis, CV as the x-axis, and the intensity of the trace as the abundance of the specified ions. These dispersion plots provide a topological representation of the differences in DMS behavior of the electrosprayed 4-ABA ions.

Tandem mass spectrometry (MS/MS) experiments were conducted using the enhanced product ion (EPI) scan mode of the QTRAP® mass spectrometer. Each MS/MS experiment was conducted under identical instrumental conditions: ions of m/z 138 were mass selected using Q1 (0.7 Th-wide isolation window) and accelerated into q2 (30 eV lab-frame collision energy, ~3 mTorr of nitrogen target gas), where fragmentation of the precursor ion could occur. After the fragment and residual precursor ions exited q2, they entered Q3 (linear ion trap), where they were collected during a fill time of 50 ms, cooled, and then mass analyzed over the range of m/z 50-145 by mass-selective axial ejection (MSAE) at a rate of 10,000 Th/s.

Hydrogen-deuterium exchange (HDX) experiments were conducted to probe the structures of the protonated 4-ABA molecules. The deuterating reagent, deuterium oxide ($D_2O$) was admitted to the junction chamber between the end of the DMS cell and the orifice of the MS by allowing the throttle gas (FIG. 17) to sample the headspace of a bottle containing 100% $D_2O$. Although the exact concentration of $D_2O$ in this region was not determined, conditions were held constant during the timeframe of the HDX experiments of each protonated 4-ABA molecule. With the SV fixed at +3500V, the CV was scanned from −15V to +15V in 0.1-V increments; at each incremental value of CV, ions were analyzed by using an enhanced mass spectra (EMS) scan. In EMS scans, a narrow band of ions (m/z 135-145) is filtered by Q1, transmitted through q2 without any fragmentation, collected in Q3 for a 10-ms fill time, and subsequently analyzed by MSAE.

NMR Spectroscopy. One-dimensional $^{13}$C and $^1$H NMR spectra were acquired on a Bruker AV-400 spectrometer (Bruker Ltd, Rheinstetten, Germany) using a 5-mm broad-band observe probe. Solvent-derived peaks (either $CD_3OD$ or $CD_3CN$) were used to calibrate the chemical shifts. Typically, a total of 1,000 transients, each of 32 k data points, was acquired with an acquisition time of 0.66 s, a 2-s interpulse delay, a spectral width of 250 ppm, with Waltz-16 $^1$H decoupling throughout the experiment. A pulse width of 3.2 μs at 0 dB (30°) was used. The free-induction decay (FID) was zero-filled by a factor of 2 and multiplied by a 2-Hz exponential line-broadening factor prior to Fourier transformation. Measured spectra were compared to library spectra for verification.

Theoretical Methods. All calculations were performed using the Gaussian 09 (revision A.1) suite of programs and the results visualized using GaussView 5.0.9. Geometry optimization of all structures was performed at the density functional (DFT) level of theory with functionals of the "pure"-DFT type; both of these used the gradient-corrected exchange functional of Becke, which was combined with either the gradient corrected correlation functional of Lee, Yang, and Parr using the cc-pVTZ basis set.

Results and Discussion. According to the applicant's teachings, two different sites of protonation for 4-ABA by ESI-DMS were generated and separated.

Figure 19:
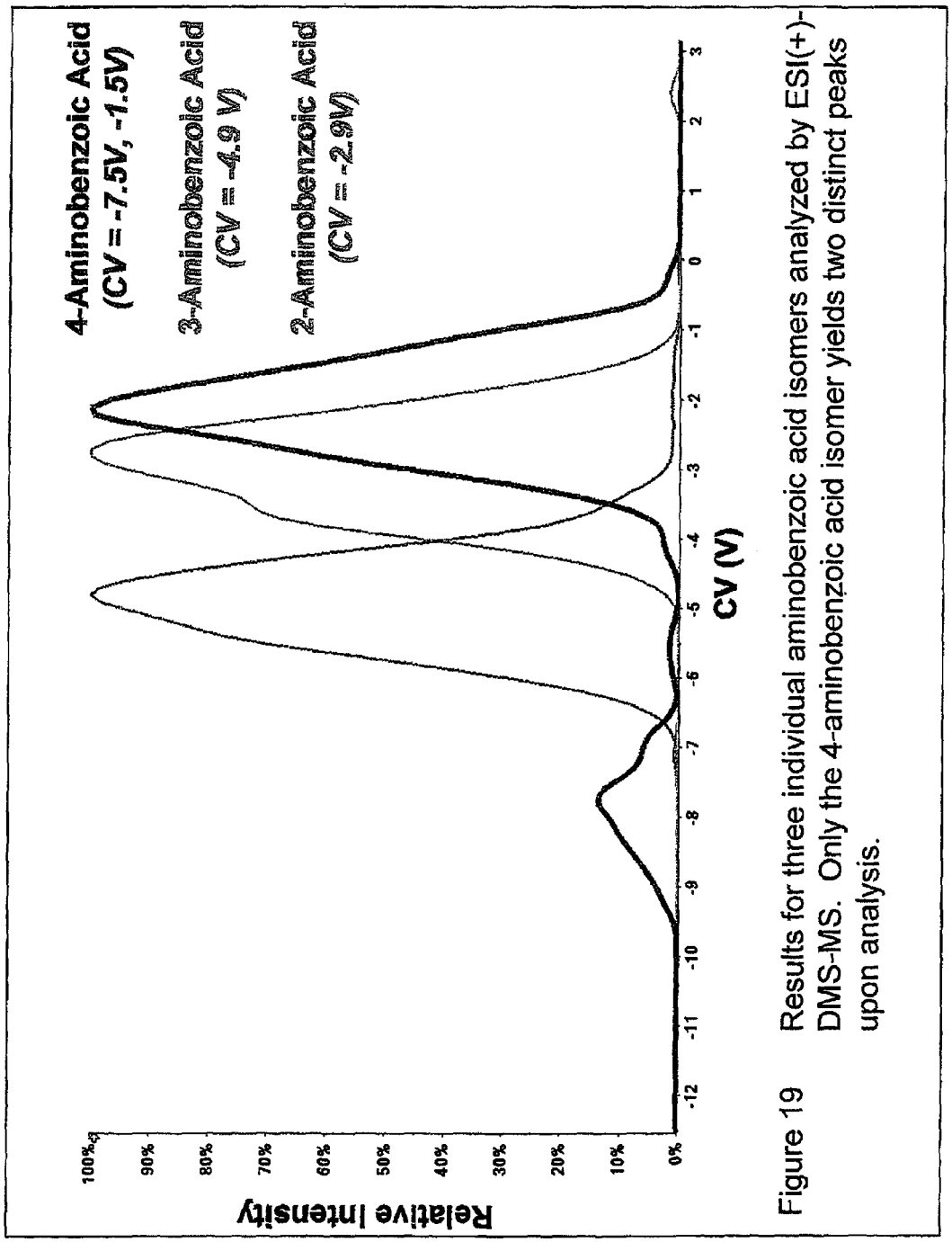
FIG. 19 shows the results for three individual aminobenzoic acid isomers analyzed by ESI(+)-DMS-MS. Only the 4-aminobenzoic acid isomer yields two distinct peaks upon analysis FIG. 20 (a) shows a DMS ionogram obtained during ESI (+)-MS/MS analysis of 4-ABA sprayed from a 100% water solution.

Typically, when low-molecular weight analytes (MW<1000 Da) are ionized by ESI(+) and analyzed using DMS, the ionized analytes are transmitted at one optimum CV (at a given SV). Essentially, one ion population provides one peak in the DMS ionogram. However, this is not the case for the ESI(+)-DMS analyses of 4-ABA solutions, which yielded two distinct peaks at CV=−7.5V and −1.5V (SV fixed at +3500V) in the DMS ionogram (FIG. 19). At these two CV values, the mass spectrometer recorded MS/MS spectra for the protonated 4-ABA ions (m/z 138) and, while there were subtle differences between these two data sets, the fragmentation patterns confirmed the presence of 4-ABA ions.

However, another possible explanation existed: the 4-ABA sample could have been contaminated with either the 2- or the 3-aminobenzoic acid isomer, both of which would provide similar MS/MS spectra from precursor ions having the same m/z value as and isomeric structures of 4-ABA. To disprove this hypothesis, we analyzed 2-ABA and 3-ABA samples independently using the same ESI(+)-DMS experiment as the 4-ABA sample. As displayed in FIG. 19, the 2-ABA (CV=−2.9V) and the 3-ABA (CV=−4.9V) yielded ionograms containing only one peak, with each peak appearing at unique CV values to the 4-ABA data. Further evidence confirming the presence of only the 4-ABA isomer was obtained by analysis using $^1$H and $^{13}$C NMR.

Figure 20:
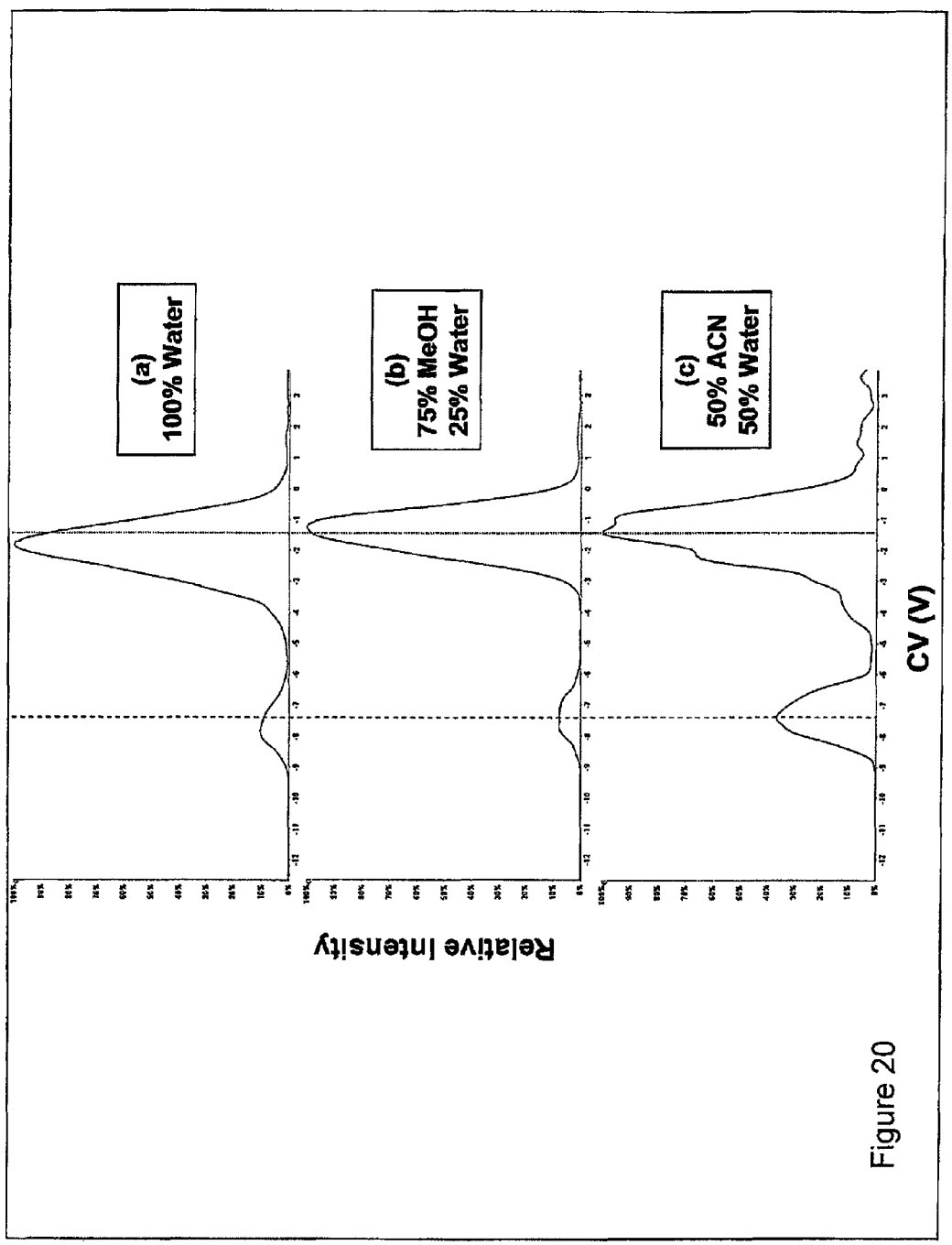
FIG. 20 (b) shows a DMS ionogram obtained during ESI (+)-MS/MS analysis of 4-ABA sprayed from a 75% methanol, 25% water solution.

Similar to previous studies, we also observed differences in the DMS behavior of protonated 4-ABA molecules produced by ESI(+) as a function of the organic solvents used. These differences lend support to the generation of 4-ABA molecules protonated at two distinct locations and their separation using DMS. For example, we analyzed solutions of 4-ABA prepared in one of three different solvent systems: (1) 100% water, (2) 75% methanol/25% water, and (3) 50% acetonitrile/50% water; solvent systems (2) and (3) are similar to those used in earlier 4-ABA studies. FIG. 20 displays the DMS ionograms obtained when we electrosprayed each of these 4-ABA solutions; in each case, two dominant peaks were produced at CV=−7.5V and CV=−1.5V. These two species were present at the same CVs regardless of the organic solvent used in the ESI(+) solution—only the relative abundance of each species changed. Given the apparent dependence of these abundances upon solvent composition, we can envision the modification of the ESI(+) solvent conditions by the addition of another solvent via a mixing tee placed before the ESI(+) source to favor the formation of one site of protonation over another.

According to the previous findings, when MeOH/H$_2$O was used as the ESI solvent system, only the O-protonated 4-ABA molecule was formed. When we analyzed a 4-ABA solution using the same solvent composition [FIG. 20(b)], we observed one DMS-separated 4-ABA ion at CV=−1.5V in vast excess (~92%) to a second 4-ABA ion at CV=−7.5V (~8%). When the Kass group analyzed an aqueous acetonitrile solvent system (50/50), they reported the formation of an estimated 70/30 mixture of O- and N-protonated 4-ABA. Interestingly, when acetonitrile was used in the ESI(+) solvent of the ESI-DMS-MS/MS experiments [FIG. 20(c)], we observed a similar ratio of 4-ABA ions transmitted at CV=−7.5V (78%) to those transmitted at CV=−1.5V (~22%). These experimental data lend support to the generation and transmission of N-protonated 4-ABA molecules at CV=−7.5V, with O-protonated 4-ABA molecules transmitted though the DMS at CV=−1.5V.

Figure 21:
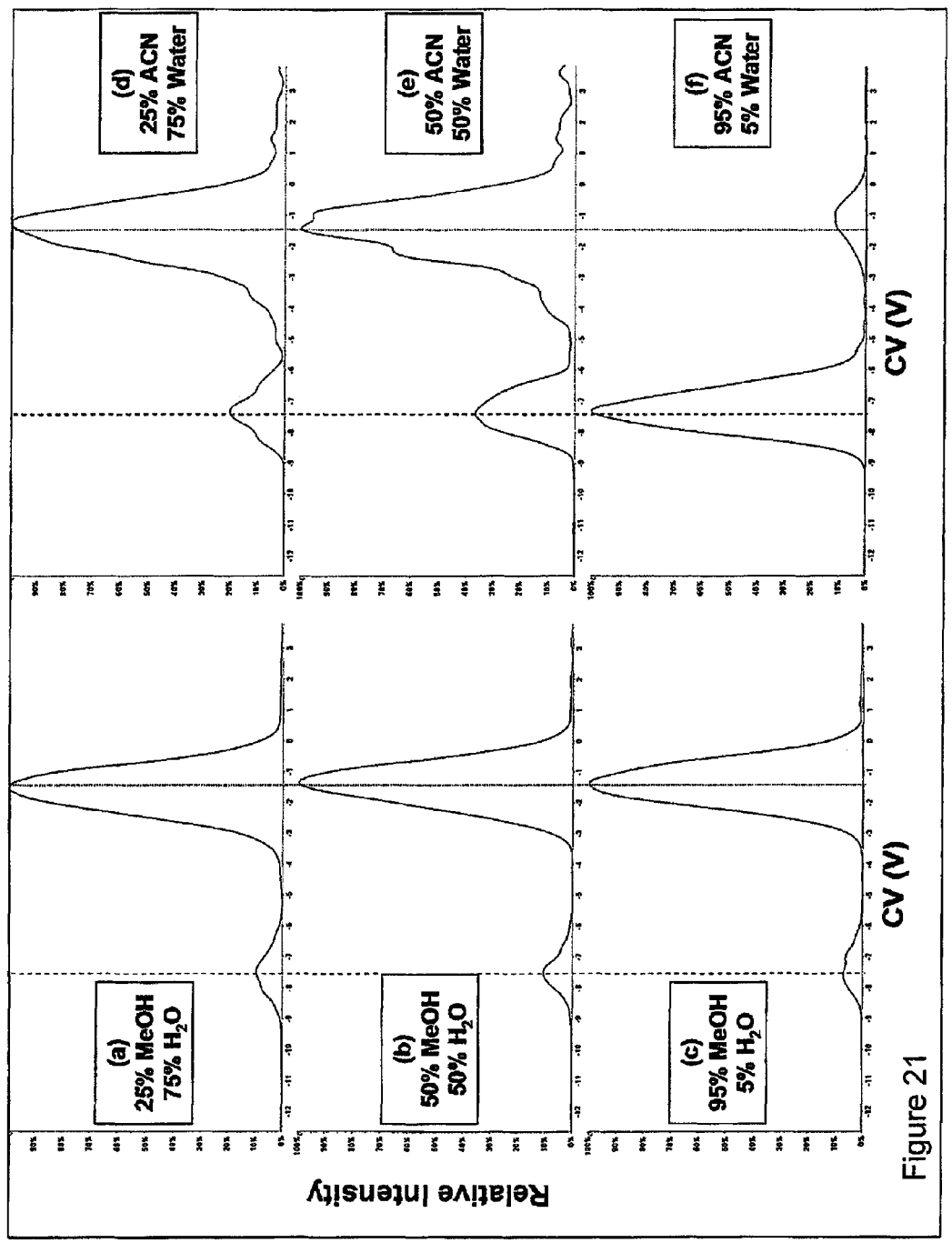
FIG. 21 (a) shows a DMS ionogram obtained during ESI (+)-MS/MS analysis of 4-ABA sprayed from a 25% methanol, 75% water solution.

We also examined other organic solvent to water ratios to obtain a more complete understanding of the influence of methanol and acetonitrile on the ESI(+)-DMS behaviour of 4-ABA. Besides analyzing a 100% water 4-ABA solution [FIG. 20(a)], we also analyzed 4-ABA solutions containing increasing percentages of organic solvent; FIG. 21(a)-(c) display the effects of increasing methanol ratios on the DMS ionogram, while FIG. 21(d)-(g) relate the effects of increasing acetonitrile ratios. The influence of the two solvents appear to run counter to one another; increasing the relative amount of methanol in the ESI(+) solvent maintain a high percentage of 4-ABA ions transmitted at CV=−1.5V (O-protonated 4-ABA), while increasing acetonitrile concentrations favor formation of 4-ABA ions transmitted at CV=−7.5V (N-protonated 4-ABA). The apparent enhanced formation of the N-protonated 4-ABA molecules when high percentages of aprotic acetonitrile is employed in the ESI(+) solvent system may be the result of the stabilization of the most stable site of protonation in the liquid-phase: the amino group. Conversely, the use of methanol and water (protic solvent systems) facilitates the stabilization of the O-protonated 4-ABA molecule upon ESI(+). Again, given the apparent dependence of these abundances upon solvent composition, we can envision the modification of the ESI(+) solvent conditions by the addition of another solvent via a mixing tee placed before the ESI(+) source to favor the formation of one site of protonation over another.

Based upon the effects of ESI(+) solvent composition alone, we observed differences in the behavior of protonated 4-ABA molecules as separated by the DMS. In all cases, two peaks were observed in the DMS ionograms, but the relative abundances changed as a function of solvent system—in agreement with previous findings. While correlating this DMS behavior to site of protonation is premature on its own, additional evidence for these findings comes from the underlying MS/MS spectra collected during the aforementioned DMS experiments.

Besides the differences observed when the ESI(+) solvent systems were altered, we also observed different fragmentation behavior for the 4-ABA ions as a function of their optimal transmission through the DMS. Specifically, the appearance of the MS/MS spectra at each specific CV value was unchanged even when ESI(+) solvent systems were altered. This revealed that the 4-ABA ions transmitted at CV=−7.5V and CV=−1.5V had structural differences consistent with different sites of protonation, and that these structures were reproducible. Upon interpretation of these spectra and comparison to similar studies' results, we find support in assigning an N-protonated structure to the 4-ABA molecules (m/z 138) transmitted through the DMS at a CV=−7.5V and an O-protonated structure to those ions transmitted at CV=−1.5V.

Figure 22:
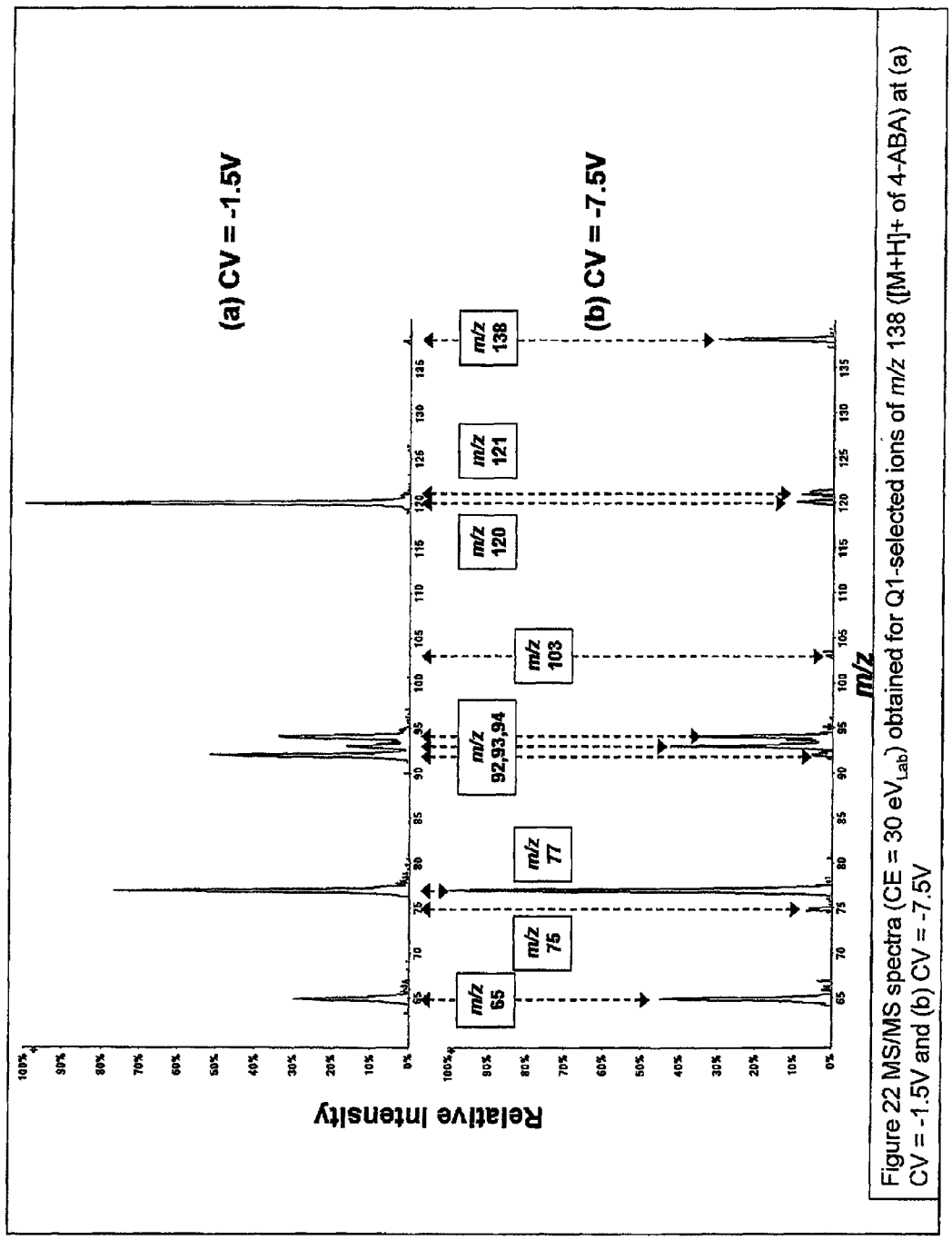
FIG. 22 (a) shows the MS/MS spectrum (CE=30 eV lab frame) obtained for Q1-selected ions of m/z 138 ([M+H]+ of 4-ABA) at CV=−1.5V.

As described earlier, MS/MS fragmentation spectra were collected for protonated 4-ABA molecules as they were transmitted through the DMS and Q mass filter, using identical instrumental conditions (e.g., same collision energy, target gas pressure, etc.). An inspection of the MS/MS spectra (FIG. 26, FIG. 22) obtained for the ions of m/z 138 transmitted through the DMS cell at CV=−1.5V [FIG. 22(a)] and at CV=−7.5V [FIG. 22(b)] shows several key differences between the two MS/MS spectra: (1) a much larger amount of residual precursor ion (m/z 138) at CV=−7.5V, (2) a very abundant m/z 120 peak (corresponding to loss of water, −18 Da) at CV=−1.5V, (3) a unique fragment ion of m/z 92 (loss of H$_2$O, CO) at CV=−1.5V, (4) unique ions of m/z 121 (loss of ammonia, −17 Da) and m/z 103 (loss of ammonia and water, −35 Da) at CV=−7.5V.

In line with the similar responses to ESI(+) solvent effects, the MS/MS spectra obtained in the present study show very similar features to those previously reported for the proposed N- and O-protonated 4-ABA molecules. For example, the larger amount of residual precursor ion (m/z 138) is present in the MS/MS spectrum at CV=−7.5V matches the reported fragmentation behavior of the N-protonated 4-ABA molecule. The lack of any residual precursor ion present in the MS/MS spectrum recorded at CV=−1.5V matches the reported fragmentation behavior of the O-protonated analogue, the same CV at which protonated 4-ABA molecules are preferentially formed and transmitted when methanol is the organic solvent used in ESI(+). In addition, while water loss (m/z 120) was reported in both the MeOH and ACN ESI MS/MS data, loss of ammonia (m/z 121) was previously reported only in the N-protonated (ACN ESI) 4-ABA molecules. Again, we see this feature for ions transmitted only at CV=−7.5V, the same ions that are preferentially formed and transmitted when ACN is the organic solvent used in ESI(+). Additionally, the unique fragment ion at m/z 103, corresponding to loss of ammonia and water, is present only at CV=−7.5V, and can be rationalized as forming after the initial loss of ammonia to form the 4-dehydrobenzoic acid cation that subsequently loses water.

Another experiment that was available for interrogating the 4-ABA ion structures with the DMS-MS instrument is gas-phase hydrogen/deuterium exchange (HDX). The findings of these experiments could be compared with previous reports of the HDX behavior of 4-ABA ions. While gas-phase HDX in mass spectrometry is typically performed on trapped ions, the ion source region itself presents a useful region for HDX given its much higher relative pressure than the vacuum region of a mass spectrometer. This higher pressure equates to increased collision rates and number densities of deuterium reagents, making the HDX reactions occur on short timescales (~ms). In addition, it is possible to switch quickly and easily between deuterating reagents (or to remove them completely) without need for instrument bake-out or pump-down times.

For the HDX experiments, we chose the throttle gas line (FIG. 17) as an introduction conduit for the deuterating reagent, deuterium oxide ($D_2O$) vapor from the headspace of a small flask containing $D_2O$. This allowed the 4-ABA ions to be separated by the DMS before interacting with the HDX reagent molecules in the region between the DMS cell and entrance into the mass spectrometer's vacuum region. Interactions between ions and neutral molecules added to the DMS cell can be utilized to promote enhanced separation by altering the clustering between these species. However, in these experiments, we wanted to focus on using the DMS to separate the 4-ABA ions based upon their native ESI(+) conditions. So, while the curtain gas can be used as a conduit for HDX reagents, the throttle gas line was employed here.

Figure 23:
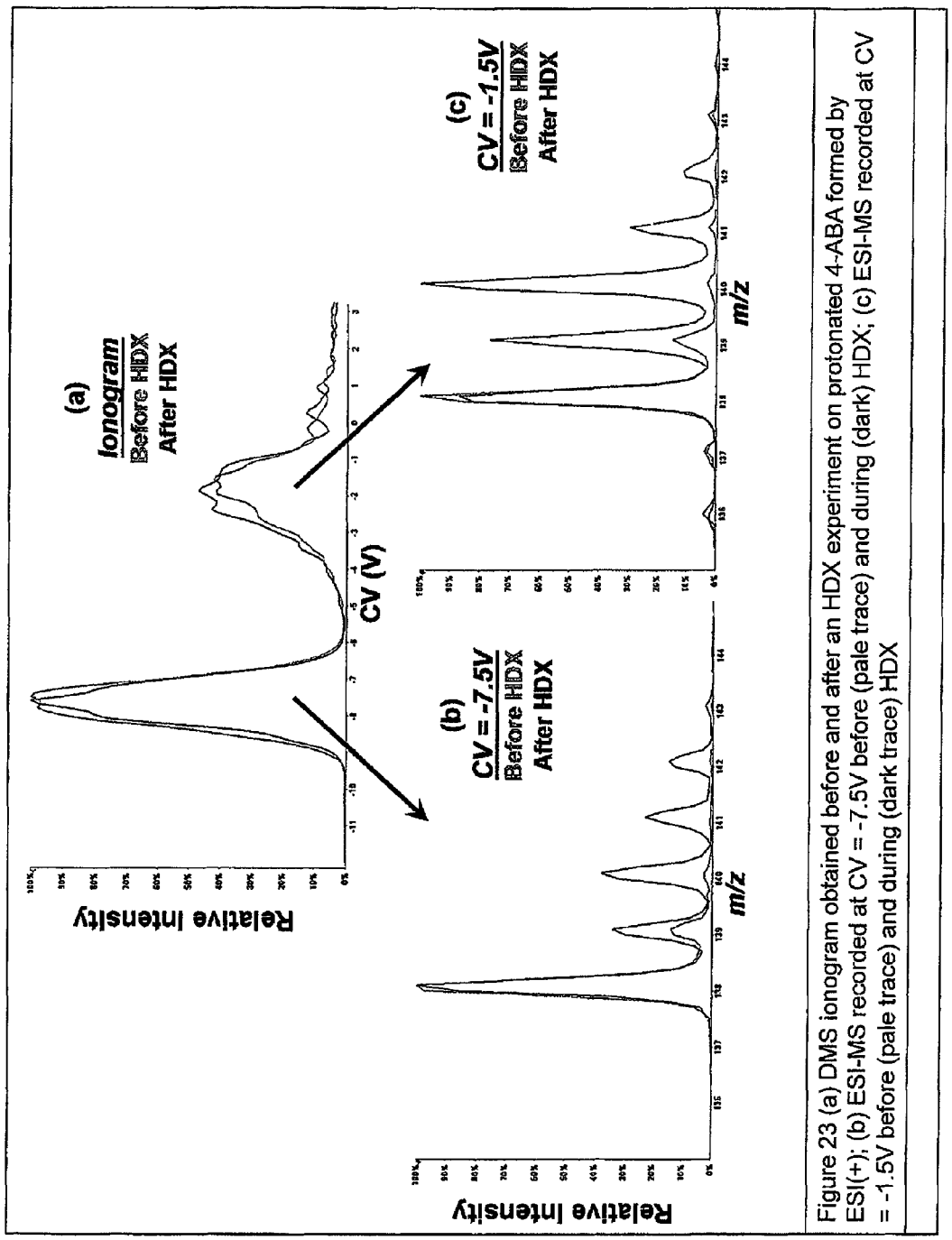
FIG. 23 (a) shows a DMS ionogram obtained before and after an HDX experiment on protonated 4-ABA formed by ESI(+).

As with the previous experiments performed with the protonated 4-ABA molecules, we observed differences between the HDX behavior of these ions as a function of their optimal DMS transmission conditions. These HDX reactivities also matched the reactivities previously assigned to the two 4-ABA protonation sites. For example, the ions of m/z 138 transmitted at CV=−7.5V showed very little incorporation of deuterium [FIG. 23(b)], in contrast to the ions of m/z 138 transmitted at CV=−1.5V, which displayed a much greater level of deuterium incorporation [FIG. 23(c)]. Given the identical reaction times and HDX reagent concentrations available to these ions, one can infer that the ions at CV=−1.5 V incorporated deuterium at a rate much faster than those ions transmitted at CV=−7.5V. Previous research into the HDX behavior of protonated 4-ABA molecules demonstrated that the N-protonated species underwent HDX at a much slower rate (~25× slower) than the O-protonated analogue. While we did not have an accurate assessment of the true number density of $D_2O$ in the post-DMS region, we can safely assume that the amount of $D_2O$ each 4-ABA ion encounters is equivalent over the time period of these experiments. These findings add further evidence to the assignments of N-protonated 4-ABA at CV=−7.5V and O-protonated 4-ABA at CV=−1.5V in the ESI-DMS data.

While the previous experiments have been generally comparative in nature, we have also examined the fundamental ion mobility behavior of the protonated 4-ABA molecules in the DMS. Analysis of these data was used to probe the properties of the different 4-ABA ions to understand why these two structures would demonstrate different DMS mobility behavior.

Figure 24:
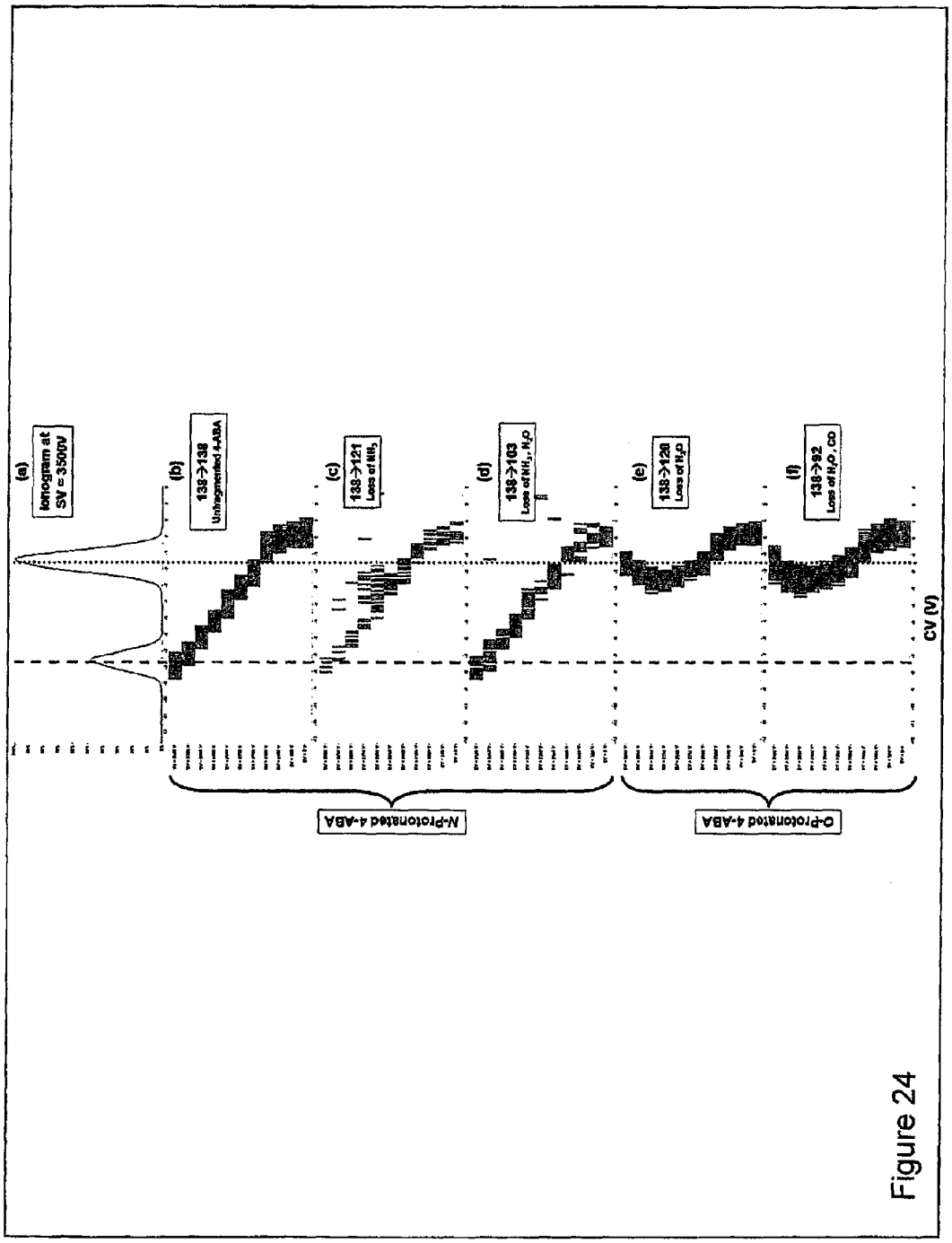
FIG. 24 (a) shows a DMS ionogram obtained during ESI (+)-MS/MS analysis of 4-ABA using an SV of +3500 and scanning CV from −15V to +15V (only −12V to +3V shown).

To evaluate the DMS mobility behavior of the 4-ABA ions, we generated dispersion plots wherein we scanned both the SV and CV are scanned synchronously while electrospraying 4-ABA solution (FIG. 24). As mentioned previously, as SV is stepped from 0 to 3500V (in 500-V increments), CV is scanned from −15 to +15V at each incremental SV value. At each CV value, an MS/MS spectrum of protonated 4-ABA was recorded. The dispersion plots are constructed with SV as the y-axis, CV as the x-axis, and the intensity of the trace as the abundance of the specified ions. These dispersion plots provide a topological representation of the differences in DMS behavior of the electrosprayed 4-ABA ions.

All of the ionograms displayed to this point in this report were recorded with a SV of +3500V, providing separation of the two 4-ABA ion populations at CV values of −7.5 V and −1.5V [FIG. 24(a)]. The intensities of these two peaks comprise the all of the ions present in the MS/MS fragmentation spectra for the 4-ABA ions (m/z 138). However, several of the fragment ions unique to the CV=−7.5V peak or the CV=−1.5V peak come from precursor ions that behave very differently in the DMS dispersion plots. For example, at low SV values, CV has little effect on the separation of ions within the DMS and most ions are transmitted near CV=0V. However, as SV is increased, the differences between the high- and low-field mobilities of ions become much greater.

By evaluating the patterns present in the dispersion plots [FIGS. 24(b)-(f)] collected for the 4-ABA ions, we discovered two distinct mobility behaviors from the protonated 4-ABA molecule populations. In each dispersion plot, we monitored the 4-ABA ions (m/z 138) that fragmented to form specific product ions (e.g., FIG. 24(c) shows the dispersion plot of all of the 4-ABA ions that fragmented to form ions of m/z 121, corresponding to loss of $NH_3$). By following the traces in each dispersion plot, we can discern two patterns of DMS behavior from these ions: (1) in FIGS. 24(b)-(d), the ion signal shifts to more negative CV values as SV is increased, ultimately settling at CV=−7.5V at the maximum SV employed (+3500V). These specific ions correspond to ions that are fragments of N-protonated 4-ABA: ions of m/z 138, corresponding to the presence of residual precursor ion in the MS/MS spectrum [FIG. 24(b)]; ions of m/z 121, which correspond to the loss of $NH_3$ from the precursor ion [FIG. 24(c)]; and ions of m/z 103, produced from the loss of $NH_3$ and $H_2O$ from the 4-ABA precursor ions [FIG. 24(d)].

In contrast, the 4-ABA ions that are present as the O-protonated form demonstrate different DMS mobility behavior in their dispersion plots. For example, the dispersion plot for 4-ABA ions that fragment via loss of $H_2O$ to form ions of m/z 120 [FIG. 24(e)] show similar curvature as the dispersion plot for the precursor ions that fragment to form ions of m/z 92 (loss of $H_2O$ and CO from the 4-ABA ion) [FIG. 24(f)]. In the analysis of the MS/MS spectra (vide supra), these fragment ions were associated with the 4-ABA ions transmitted at CV=−1.5V—the O-protonated 4-ABA molecules. These 4-ABA ions show an initial shift toward negative CV values with increasing SV, then curve back to more positive CV values.

We postulate that the observed differences in DMS mobility behavior can be categorized and associated with the structural features of the different protonated 4-ABA molecules. The dispersion plots presented in FIGS. 24(b), (c), and (d) display the behavior of ions exhibiting Type A behavior, where the optimal CV becomes more negative with ever increasing SV. Conversely, the dispersion plots in FIGS. 24(e) and (f) demonstrate Type B behavior, with the optimal CV initially trending negative with increasing SV, but ultimately becoming more positive with increasing SV. The Type A behavior is associated with the N-protonated 4-ABA molecules, which can be rationalized with the aid of computational modeling to examine the structures and electronic properties of the protonated 4-ABA molecules. The N-protonated 4-ABA structure [FIG. 25(a)] shows an expected structure where no resonance stabilization of the positive charge is afforded by the rest of the molecule. The calculated dipole moment for this ion (13.08 Debye), as indicated by the blue arrow, shows a strong dipole in the region of the protonated amino group. Conversely, the calculated structure for 4-ABA molecules protonated at the carboxylic acid group [FIG. 25(b)] reveals an ion that exhibits resonance stabilization of the positive charge throughout the aromatic ring, as well the amino group. Accordingly, the calculated structure of the O-protonated 4-ABA molecule has a smaller dipole moment (1.47 Debye) than the N-protonated analogue.

While the role of chemical modifier polarity and dipole moments have been considered in DMS, neither the role of the ion's site of protonation (charging) nor its dipole moment have been extensively evaluated. In the case of the protonated 4-ABA molecules, when the positive charge is localized at the amino group (N-protonated), we surmise that the clustering of residual ESI solvent and/or ambient $N_2$ gas molecules should occur mainly at the charged ammonium group. The stronger dipole moment for the N-protonated 4-ABA molecules is expected to provide more of a polarization effect to the transport gas. This is expected to promote clustering between the ion and the background gas. Clustering suppresses the low-field mobility for these ions and leads to Type A behavior due to the dynamic clustering/declustering of these species. For the O-protonated 4-ABA molecules, a different scenario exists given the resonance stabilized structure for this ion. This leads to the smaller calculated dipole moment for the O-protonated analogue, which we postulate reduces the clustering interactions of the ion with the transport gas within the DMS cell. With increasing SV (i.e., where the high-field mobility regime dominates), behavior of these ions exhibits more "hard sphere" characteristics (i.e., more Type C character) as the clustering interactions with solvent and background gas play a much reduced role. Again, given the apparent dependence of these abundances upon solvent composition, we can envision the modification of the ESI(+) solvent conditions by the addition of another solvent via a mixing tee placed before the ESI(+) source to favor the formation of one site of protonation over another.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

While the applicant's teachings have been particularly shown and described with reference to specific illustrative embodiments, it should be understood that various changes in form and detail may be made without departing from the spirit and scope of the teachings. Therefore, all embodiments that come within the scope and spirit of the teachings, and equivalents thereto, are claimed. The descriptions and diagrams of the methods of the applicants' teachings should not be read as limited to the described order of elements unless stated to that effect.

While the applicant's teachings have been described in conjunction with various embodiments and examples, it is not intended that the applicant's teachings be limited to such embodiments or examples. On the contrary, the applicant's teachings encompass various alternatives, modifications, and equivalents, as will be appreciated by those of skill in the art, and all such modifications or variations are believed to be within the sphere and scope of the invention.

The invention claimed is:

1. An electrospray ion source system for detecting emitter failure comprising:
    a liquid chromatography column suitable for chromatographic separation of a sample;
    the column having an inlet for receiving the sample; and an outlet for ejecting the sample;
    a make-up flow channel for introducing a make-up flow of liquid to the sample post-column, wherein the make-up flow normalizes the spray current;
    an electrospray ionization source having one or more emitter nozzles for receiving the make-up flow containing sample;
    a power supply for providing a voltage to the one or more emitter nozzles; and
    a measurement device for measuring and monitoring the spray current of the one or more emitter nozzles.

2. The system of claim 1 wherein the liquid chromatography column is micromachined on a first substrate.

3. The system of claim 2 wherein the make-up flow channel is micromachined on a second substrate.

4. The system of claim 3 further comprising a connector for connecting the first substrate to the second substrate.

5. The system of claim 1 wherein the make-up flow is a one of a dilute electrolyte and a solvent without electrolyte.

6. The system of claim 1 wherein the make-up flow channel comprises a tee junction.

7. The system of claim 4 wherein the one or more nozzles comprises one or more array of emitters.

8. The system of claim 7 comprising replacing the array of emitters or one or more of the plurality of the array of emitters when the spray current exceeds the normalized spray current limits indicating nozzle failure.

9. The system of claim 4 wherein the connector comprises a transfer capillary.

10. The system of claim 1 wherein the measurement device comprises an ammeter.

11. The system of claim 7 further comprising a positioning device for positioning the array of emitters or one or more of the plurality of the array of emitters.

12. The system of claim 1 further comprising a mass spectrometer for analyzing the spray from one or more emitter nozzles.

13. A method for detecting emitter failure comprising:
    providing liquid chromatography column suitable for chromatographic separation of a sample; the column having an inlet for receiving the sample; and an outlet for ejecting the sample;
    providing a make-up flow channel for introducing a make-up flow of liquid to the sample post-column, wherein the make-up flow normalizes the spray current;
    providing an electrospray ionization source having one or more emitter nozzles for receiving the make-up flow containing sample;
    providing a power supply for providing a voltage to the one or more emitter nozzles; and
    providing a measurement device for measuring and monitoring the spray current of the one or more emitter nozzles.

14. An electrospray ion source system for altering the site of protonation of ions comprising:
    a liquid chromatography column suitable for chromatographic separation of a sample;
    the column having an inlet for receiving the sample; and an outlet for ejecting the sample;
    a make-up flow channel for introducing a make-up flow of liquid to the sample post-column, wherein the make-up flow alters the site of protonation of ions; an electrospray ionization source having one or more emitter nozzles for receiving the make-up flow containing sample; and a power supply for providing a voltage to the one or more emitter nozzles.

15. The system of claim 14 further comprising a differential ion mobility spectrometer for separating the ions.

16. The system of claim 14 wherein the make-up flow channel comprises a tee junction.

17. The system of claim 14 wherein the one or more nozzles comprises one or more array of emitters.

18. The system of claim 14 wherein the liquid chromatography column is micromachined on a first substrate; the make up flow channel is micromachined on a second substrate and a transfer capillary connects the first substrate to the second substrate.

19. The system of claim 17 further comprising a positioning device for positioning the array of emitters or one or more of the plurality of the array of emitters.

20. The system of claim 15 further comprising a mass spectrometer for analyzing the ions from the differential mass spectrometer.

\* \* \* \* \*